(12) United States Patent
van Rijn et al.

(10) Patent No.: US 7,312,030 B2
(45) Date of Patent: Dec. 25, 2007

(54) ADAPTATION SITES OF PORCINE REPRODUCTIVE AND RESPIRATORY SYNDROME VIRUS

(75) Inventors: Petrus Antonius van Rijn, Lelystad (NL); Johanna Jacoba M. Meulenberg, Amsterdam (NL)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 542 days.

(21) Appl. No.: 10/407,822

(22) Filed: Apr. 4, 2003

(65) Prior Publication Data

US 2003/0219732 A1    Nov. 27, 2003

(30) Foreign Application Priority Data

Apr. 5, 2002   (EP)   ................. 02076334

(51) Int. Cl.
*C12N 7/01*    (2006.01)
*C12N 7/04*    (2006.01)
*C07K 14/08*    (2006.01)

(52) U.S. Cl. ................ 435/5; 435/235.1; 435/373
(58) Field of Classification Search ................ 435/69.1
See application file for complete search history.

(56) References Cited

OTHER PUBLICATIONS

Welch S. et al. Construction and evaluation of genetically engineered replication-defective porcine reproductive and respiratorysyndrome virus vaccine candidates. (2004) Veterinary immunology and immunopathology. vol. 102, p. 277-290.*
Lazar et al. Transforming Growth Factor alpha: Mutation of aspartic acid 47 and leucine 48 results in different biological activities. (1988) Molecular and cellular biology, vol. 8, p. 1247-1252.*
Brurgess W. et al. Pissible dissociation of the heparin-binding and mitogenic activities of heparin-binding (Acidic Fibroblast) growth factor-1 from its receptor-binding activities by site-directed mutagenesis of a single lysine residue. (1990) vol. 111, p. 2129-2138.*
Bowie et al. Science, 1990, vol. 247. p. 1306-1310.*
Allende et al., Mutations in the genome of procine reproductive and respiratory syndrome virus responsible for the attenuation phenotype, Archives of Virology, 2000, pp. 1149-1161, vol. 145.
Funkhouser et al., Mutations in the 5'-noncoding, 2C, and P3 Regions of the Genome Increase the Efficiency of Hepatitis A Virus Growth in MRC-5 Cells, Vaccines 1994, pp. 345-349, Cold Spring Harbor Laboratory Press.
Meulenberg et al., Infectious Transcripts from Cloned Genome-Length cDNA of Porcine Reproductive and Respiratory Syndrome Virus, Jounal of Virology, Jan. 1998, pp. 380-387, vol. 72, No. 1, American Society for Microbiology.
Meulenberg et al., Molecular characterization of Lelystad virus, Veterinary Microbiology, 1997, pp. 197-202, vol. 55.
Snijder et al., The molecular biology of arteriviruses, Journal of General Virology, 1998, pp. 961-979, vol. 79.

* cited by examiner

*Primary Examiner*—Bruce R. Campell
*Assistant Examiner*—Agnieszka Boesen
(74) *Attorney, Agent, or Firm*—Michael Morris; Thomas Blankinship; Mary-Ellen Devlin

(57) ABSTRACT

A method for determining the capability of an arterivirus to replicate in a permissive cell is disclosed. The method includes determining an amino acid at a position that corresponds to an amino acid of a protein of a porcine reproductive and respiratory syndrome virus. The invention also discloses a method for determining the capability of an arterivirus to replicate in a green monkey cell line. The invention further discloses a method for producing arterivirus in a green monkey cell line wherein the virulence of the arterivirus is maintained and the virus yield is increased. Methods for determining the attenuation of an arterivirus and for attenuating the virulence of the arterivirus by changing amino acids are further disclosed.

3 Claims, 6 Drawing Sheets

Growth curves of vABV437, LV4.2.1, vABV688, vABV772 and vABV773 on Marc-145

Legend:
- ♦ 437
- ■ LV4.2.1
- × vABV688
- △ vABV772
- ∗ vABV773

X-axis: Hours post infectionn
Y-axis: Log TCID50/ml

Fig. 2A

Growth curves of vABV437, LV4.2.1, vABV688, vABV772 and vABV773 on PAMs

Fig. 2B ical field, and more particularly, to the field of vaccine production. More specifically, the invention relates to the in vitro propagation of virus and to the adaptation of a virus to a cell line and the attenuation of a virus.

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial sequence
<220> FEATURE:
<223> OTHER INFORMATION: Synthesized sequence, primer

<400> SEQUENCE: 1
tctaggaatt ctagacgatc gt                                              22

<210> SEQ ID NO 2
<211> LENGTH: 20
<212> TYPE: DNA
<213> ORGANISM: Artificial sequence
```

-continued

```
<220> FEATURE:
<223> OTHER INFORMATION: Synthesized sequence, primer

<400> SEQUENCE: 2
ctgccgcccg ggcaagtgcc                                          20

<210> SEQ ID NO 3
<211> LENGTH: 19
<212> TYPE: DNA
<213> ORGANISM: Artificial sequence
<220> FEATURE:
<223> OTHER INFORMATION: Synthesized sequence, primer

<400> SEQUENCE: 3
cataataacc ctcaagttg                                           19

<210> SEQ ID NO 4
<211> LENGTH: 15111
<212> TYPE: DNA
<213> ORGANISM: Lelystad virus
<300> PUBLICATION INFORMATION:
<308> DATABASE ACCESSION NUMBER: Genbank/M96262
<309> DATABASE ENTRY DATE: 2000-11-08

<400> SEQUENCE: 4
atgatgtgta gggtattccc cctacataca cgacacttct agtgtttgtg taccttggag      60
gcgtgggtac agccccgccc cacccccttgg cccctgttct agcccaacag gtatccttct    120
ctctcggggc gagtgcgccg cctgctgctc ccttgcagcg ggaaggacct cccgagtatt     180
tccggagagc acctgcttta cgggatctcc accctttaac catgtctggg acgttctccc     240
ggtgcatgtg caccccggct gcccgggtat tttggaacgc cggccaagtc ttttgcacac     300
ggtgtctcag tgcgcggtct cttctctctc cagagcttca ggacactgac ctcggtgcag     360
ttggcttgtt ttacaagcct agggacaagc ttcactggaa agtccctatc ggcatccctc     420
aggtggaatg tactccatcc gggtgctgtt ggctctcagc tgttttccct ttggcgcgta     480
tgacctccgg caatcacaac ttcctccaac gacttgtgaa ggttgctgat gttttgtacc     540
gtgacggttg cttggcacct cgacaccttc gtgaactcca agtttacgag cgcggctgca     600
actggtaccc gatcacgggg cccgtgcccg ggatgggttt gtttgcgaac tccatgcacg     660
tatccgacca gccgttccct ggtgccaccc atgtgttgac taactcgcct ttgcctcaac     720
aggcttgtcg gcagccgttc tgtccatttg aggaggctca ttctagcgtg tacaggtgga     780
agaaatttgt ggttttcacg gactcctccc tcaacggtcg atctcgcatg atgtggacgc     840
cggaatccga tgattcagcc gccctggagg tactaccgcc tgagttagaa cgtcaggtcg     900
aaatcctcat tcggagtttt cctgctcatc accctgtcga cctggccgac tgggagctca     960
ctgagtcccc tgagaacggt tttccttca acacgtctca ttcttgcggt caccttgtcc     1020
agaaccccga cgtgtttgat ggcaagtgct ggctctcctg ctttttgggc cagtcggtcg    1080
aagtgcgctg ccatgaggaa catctagctg acgccttcgg ttaccaaacc aagtggggcg    1140
tgcatggtaa gtacctccag cgcaggcttc aagttcgcgg cattcgtgct gtagtcgatc    1200
ctgatggtcc cattcacgtt gaagcgctgt cttgccccca gtcttggatc aggcacctga    1260
ctctggatga tgatgtcacc ccaggattcg ttcgcctgac atcccttcgc attgtgccga    1320
acacagagcc taccacttcc cggatctttc ggtttggagc gcataagtgg tatggcgctg    1380
ccggcaaacg ggctcgtgct aagcgtgccg ctaaaagtga gaaggattcg gctcccaccc    1440
ccaaggttgc cctgccggtc cccacctgtg gaattaccac ctactctcca ccgacagacg    1500
```

-continued

```
ggtcttgtgg ttggcatgtc cttgccgcca taatgaaccg gatgataaat ggtgacttca    1560
cgtcccctct gactcagtac aacagaccag aggatgattg ggcttctgat tatgatcttg    1620
ttcaggcgat tcaatgtcta cgactgcctg ctaccgtggt tcggaatcgc gcctgtccta    1680
acgccaagta ccttataaaa cttaacggag ttcactggga ggtagaggtg aggtctggaa    1740
tggctcctcg ctccctttct cgtgaatgtg tggttggcct ttgctctgaa ggctgtgtcg    1800
caccgcctta tccagcagac gggctaccta acgtgcact cgaggccttg gcgtctgctt    1860
acagactacc ctccgattgt gttagctctg gtattgctga cttttcttgct aatccacctc    1920 ctcaggaatt ctggaccctc gacaaaatgt tgacctcccc gtcaccagag cggtccggct    1980
tctctagttt gtataaatta ctattagagg ttgttccgca aaaatgcggt gccacggaag    2040
gggctttcat ctatgctgtt gagaggatgt tgaaggattg tccgagctcc aaacaggcca    2100
tggcccttct ggcaaaaatt aaagttccat cctcaaaggc cccgtctgtg tccctggacg    2160
agtgtttccc tacggatgtt ttagccgact tcgagccagc atctcaggaa aggccccaaa    2220
gttccggcgc tgctgttgtc ctgtgttcac cggatgcaaa agagttcgag gaagcagccc    2280
cggaagaagt tcaagagagt ggccacaagg ccgtccactc tgcactcctt gccgagggtc    2340
ctaacaatga gcaggtacag gtggttgccg gtgagcaact gaagctcggc ggttgtggtt    2400
tggcagtcgg gaatgctcat gaaggtgctc tggtctcagc tggtctaatt aacctggtag    2460
gcggaatttt gtcccctca gaccccatga agaaaacat gctcaatagc cgggaagacg    2520
aaccactgga tttgtcccaa ccagcaccag cttccacaac gacccttgtg agagagcaaa    2580
cacccgacaa cccaggttct gatgccggtg ccctccccgt caccgttcga gaatttgtcc    2640
cgacggggcc tatactctgt catgttgagc actgcggcac ggagtcgggc gacagcagtt    2700
cgcctttgga tctatctgat gcgcaaaccc tggaccagcc tttaaatcta tccctggccg    2760
cttggccagt gagggccacc gcgtctgacc ctggctgggt ccacgtagg cgcgagcctg    2820 tctttgtaaa gcctcgaaat gctttctctg atggcgattc agcccttcag ttcggggagc    2880
tttctgaatc cagctctgtc atcgagtttg accggacaaa agatgctccg gtggttgacg    2940
cccctgtcga cttgacgact tcgaacgagg ccctctctgt agtcgatcct ttcgaatttg    3000
ccgaactcaa gcgcccgcgt ttctccgcac aagccttaat tgaccgaggc ggtccacttg    3060
ccgatgtcca tgcaaaaata aagaaccggg tatatgaaca gtgcctccaa gcttgtgagc    3120
ccggtagtcg tgcaaccca gccaccaggg agtggctcga caaaatgtgg gatagggtgg    3180
acatgaaaac ttggcgctgc acctcgcagt tccaagctgg tcgcattctt gcgtccctca    3240
aattcctccc tgacatgatt caagacacac cgcctcctgt tcccaggaag aaccgagcta    3300
gtgacaatgc cggcctgaag caactggtgg cacagtggga taggaaattg agtgtgaccc    3360
cccccccaaa accggttggg ccagtgcttg accagatcgt ccctccgcct acggatatcc    3420
agcaagaaga tgtcaccccc tccgatgggc cacccatgc gccggatttt cctagtcgag    3480
tgagcacggg cggagttgg aaaggcctta tgctttccgg cacccgtctc gcggggtcta    3540
tcagccagcg ccttatgaca tgggttttttg aagttttctc ccacctccca gcttttatgc    3600
tcacactttt ctcgccgcgg ggctctatgg ctccaggtga ttggttgttt gcaggtgtcg    3660
ttttacttgc tctcttgctc tgtcgttctt acccgatact cggatgcctt cccttattgg    3720
gtgtcttttc tggttctttg cggcgtgttc gtctgggtgt ttttggttct tggatggctt    3780
ttgctgtatt tttattctcg actccatcca acccagtcgg ttcttcttgt gaccacgatt    3840
```

```
cgccggagtg tcatgctgag cttttggctc ttgagcagcg ccaactttgg gaacctgtgc   3900
gcggccttgt ggtcggcccc tcaggcctct tatgtgtcat tcttggcaag ttactcggtg   3960
ggtcacgtta tctctggcat gttctcctac gtttatgcat gcttgcagat ttggcccttt   4020
ctcttgttta tgtggtgtcc cagggggcgtt gtcacaagtg ttggggaaag tgtataagga   4080
cagctcctgc ggaggtggct cttaatgtat ttccttctc gcgcgccacc cgtgtctctc     4140
ttgtatcctt gtgtgatcga ttccaaacgc caaaagggt tgatcctgtg cacttggcaa    4200
cgggttggcg cgggtgctgg cgtggtgaga gccccatcca tcaaccacac caaaagccca   4260
tagcttatgc caatttggat gaaaagaaaa tgtctgccca acggtggtt gctgtcccat     4320 acgatcccag tcaggctatc aaatgcctga agttctgca ggcgggaggg gccatcgtgg    4380
accagcctac acctgaggtc gttcgtgtgt ccgagatccc cttctcagcc ccattttcc     4440 caaaagttcc agtcaaccca gattgcaggg ttgtggtaga ttcggacact tttgtggctg   4500
cggttcgctg cggttactcg acagcacaac tggttctggg ccggggcaac tttgccaagt   4560
taaatcagac ccccccagg aactctatct ccaccaaaac gactggtggg gcctcttaca   4620
cccttgctgt ggctcaagtg tctgcgtgga ctcttgttca tttcatcctc ggtctttggt   4680
tcacatcacc tcaagtgtgt ggccgaggaa ccgctgaccc atggtgttca aatcctttt     4740 catatcctac ctatggcccc ggagttgtgt gctcctctcg actttgtgtg tctgccgacg   4800
gggtcaccct gccattgttc tcagccgtgg cacaactctc cggtagagag gtgggggattt   4860 ttattttggt gctcgtctcc ttgactgctt tggcccaccg catggctctt aaggcagaca   4920
tgttagtggt cttttcggct ttttgtgctt acgcctggcc catgagctcc tggttaatct   4980
gcttctttcc tatactcttg aagtgggtta cccttcaccc tcttactatg ctttgggtgc   5040
actcattctt ggtgttttgt ctgccagcag ccggcatcct ctcactaggg ataactggcc   5100
ttctttgggc aattggccgc tttacccagg ttgccggaat tattacacct tatgacatcc   5160
accagtacac ctctgggcca cgtggtgcag ctgctgtggc cacagcccca gaaggcactt   5220
atatggccgc cgtccggaga gctgctttaa ctgggcgaac tttaatcttc accccgtctg   5280
cagttggatc ccttctcgaa ggtgctttca ggactcataa accctgcctt aacaccgtga   5340
atgttgtagg ctcttccctt ggttccggag gggttttcac cattgatggc agaagaactg   5400
tcgtcactgc tgcccatgtg ttgaacggcg acacagctag agtcaccggc gactcctaca   5460
accgcatgca cactttcaag accaatggtg attatgcctg gtcccatgct gatgactggc   5520
agggcgttgc ccctgtggtc aaggttgcga agggtaccg cggtcgtgcc tactggcaaa   5580
catcaactgg tgtcgaaccc ggtatcattg gggaagggtt cgccttctgt tttactaact   5640
gcggcgattc ggggtcaccc gtcatctcag aatctggtga tcttattgga atccacaccg   5700
gttcaaacaa acttggttct ggtcttgtga caaccctga aggggagacc tgcaccatca   5760
aagaaaccaa gctctctgac cttttccagac attttgcagg cccaagcgtt cctcttgggg   5820
acattaaatt gagtccggcc atcatccctg atgtaacatc cattccgagt gacttggcat   5880
cgctcctagc ctccgtccct gtagtggaag gcggcctctc gaccgttcaa cttttgtgtg   5940 tcttttttcct tctctggcgc atgatgggcc atgcctggac acccattgtt gccgtgggct   6000
tctttttgct gaatgaaatt cttccagcag ttttggtccg agccgtgttt ctttttgcac   6060 tcttttgtgct tgcatgggcc accccctggt ctgcacaggt gttgatgatt agactcctca   6120
cggcatctct caaccgcaac aagctttctc tggcgttcta cgcactcggg ggtgtcgtcg   6180
gtttggcagc tgaaatcggg acttttgctg gcagattgtc tgaattgtct caagctcttt   6240
```

```
cgacatactg cttcttacct agggtccttg ctatgaccag ttgtgttccc accatcatca   6300
ttggtggact ccatacccctc ggtgtgattc tgtggttatt caaataccgg tgcctccaca   6360
acatgctggt tggtgatggg agttttcaa gcgccttctt cctacggtat tttgcagagg   6420
gtaatctcag aaaaggtgtt tcacagtcct gtggcatgaa taacgagtcc ctaacggctg   6480
ctttagcttg caagttgtca caggctgacc ttgattttttt gtccagctta acgaacttca   6540
agtgctttgt atctgcttca aacatgaaaa atgctgccgg ccagtacatt gaagcagcgt   6600
atgccaaggc cctgcgccaa gagttggcct ctctagttca gattgacaaa atgaaaggag   6660
ttttgtccaa gctcgaggcc tttgctgaaa cagccacccc gtcccttgac ataggtgacg   6720
tgattgttct gcttgggcaa catcctcacg gatccatcct cgatattaat gtggggactg   6780
aaggaaaaac tgtgtccgtg caagagaccc ggagcctagg cggctccaaa ttcagtgttt   6840
gtactgtcgt gtccaacaca cccgtggacg ccttgaccgg catcccactc cagacaccaa   6900
cccctctttt tgagaatggt ccgcgtcatc gcagcgagga agacgatctt aaagtcgaga   6960
ggatgaagaa acactgtgta tccctcggct tccacaacat caatggcaaa gtttactgca   7020
aaatttggga caagtctacc ggtgacacct tttacacgga tgattcccgg tacacccaag   7080
accatgcttt tcaggacagg tcagccgact acagagacag ggactatgag ggtgtgcaaa   7140
ccacccccca acaggggattt gatccaaagt ctgaaacccc tgttggcact gttgtgatcg   7200
gcggtattac gtataacagg tatctgatca aggtaagga ggttctggtc cccaagcctg   7260
acaactgcct tgaagctgcc aagctgtccc ttgagcaagc tctcgctggg atgggccaaa   7320
cttgcgacct tacagctgcc gaggtggaaa agctaaagcg catcattagt caactccaag   7380 gttttgaccac tgaacaggct ttaaactgtt agccgccagc ggcttgaccc gctgtggccg   7440
cggcggccta gttgtgactg aaacggcggt aaaaattata aaataccaca gcagaacttt   7500
caccttaggc ccttttagacc taaaagtcac ttccgaggtg gaggtaaaga atcaactga   7560 gcagggccac gctgttgtgg caaacttatg ttccggtgtc atcttgatga acctcacccc   7620 accgtcccctt gtcgacgttc ttctgaaacc cggacttgac acaatacccg gcattcaacc   7680
agggcatggg gccgggaata tgggcgtgga cggttctatt tgggattttg aaaccgcacc   7740
cacaaaggca gaactcgagt tatccaagca aataatccaa gcatgtgaag ttaggcgcgg   7800
ggacgccccg aacctccaac tcccttacaa gctctatcct gttagggggg atcctgagcg   7860
gcataaaggc cgccttatca ataccaggtt tggagattta ccttacaaaa ctcctcaaga   7920
caccaagtcc gcaatccacg cggcttgttg cctgcacccc aacgggccc ccgtgtctga   7980 tggtaaatcc acactaggta ccactcttca acatggtttc gagctttatg tccctactgt   8040
gccctatagt gtcatggagt accttgattc acgccctgac accccttttta tgtgtactaa   8100 acatggcact tccaaggctg ctgcagagga cctccaaaaa tacgacctat ccacccaagg   8160
atttgtcctg cctggggtcc tacgcctagt acgcagattc atctttggcc atattggtaa   8220
ggcgccgcca ttgttcctcc catcaaccta tcccgccaag aactctatgg cagggatcaa   8280
tggccagagg ttcccaacaa aggacgttca gagcatacct gaaattgatg aaatgtgtgc   8340
ccgcgctgtc aaggagaatt ggcaaactgt gacaccttgc accctcaaga acagtactgt   8400
ttccaagccc aaaaccagga ccatcctggg caccaacaac tttattgcct tggctcacag   8460
atcggcgctc agtggtgtca cccaggcatt catgaagaag gcttggaagt ccccaattgc   8520 cttgggggaaa aacaaattca aggagctgca ttgcactgtc gccggcaggt gtcttgaggc   8580
```

-continued

| | | | | |
|---|---|---|---|---|
| cgacttggcc | tcctgtgacc | gcagcacccc | cgccattgta | agatggtttg | ttgccaacct | 8640 |
| cctgtatgaa | cttgcaggat | gtgaagagta | cttgcctagc | tatgtgctta | attgctgcca | 8700 |
| tgacctcgtg | gcaacacagg | atggtgcctt | cacaaaacgc | ggtggcctgt | cgtccgggga | 8760 |
| ccccgtcacc | agtgtgtcca | acaccgtata | ttcactggta | atttatgccc | agcacatggt | 8820 |
| attgtcggcc | ttgaaaatgg | gtcatgaaat | tggtcttaag | ttcctcgagg | aacagctcaa | 8880 |
| gttcgaggac | ctccttgaaa | ttcagcctat | gttggtatac | tctgatgatc | ttgtcttgta | 8940 |
| cgctgaaaga | cccacatttc | caattacca | ctggtgggtc | gagcaccttg | acctgatgct | 9000 |
| gggtttcaga | acgacccaa | agaaaaccgt | cataactgat | aaacccagct | tcctcggctg | 9060 |
| cagaattgag | gcagggcgac | agctagtccc | caatcgcgac | cgcatcctgg | ctgctcttgc | 9120 |
| atatcacatg | aaggcgcaga | acgcctcaga | gtattatgcg | tctgctgccg | caatcctgat | 9180 |
| ggattcatgt | gcttgcattg | accatgaccc | tgagtggtat | gaggacctca | tctgcggtat | 9240 |
| tgcccggtgc | gcccgccagg | atggttatag | cttcccaggt | ccggcatttt | tcatgtccat | 9300 |
| gtgggagaag | ctgagaagtc | ataatgaagg | gaagaaattc | cgccactgcg | gcatctgcga | 9360 |
| cgccaaagcc | gactatgcgt | ccgcctgtgg | gcttgatttg | tgtttgttcc | attcgcactt | 9420 |
| tcatcaacac | tgccctgtca | ctctgagctg | cggtcaccat | gccggttcaa | aggaatgttc | 9480 |
| gcagtgtcag | tcacctgttg | gggctggcag | atcccctctt | gatgccgtgc | taaaacaaat | 9540 |
| tccatacaaa | cctcctcgta | ctgtcatcat | gaaggtgggt | aataaaacaa | cggccctcga | 9600 |
| tccggggagg | taccagtccc | gtcgaggtct | cgttgcagtc | aagagggta | ttgcaggcaa | 9660 |
| tgaagttgat | ctttctgatg | gggactacca | agtggtgcct | cttttgccga | cttgcaaaga | 9720 |
| cataaacatg | gtgaaggtgg | cttgcaatgt | actactcagc | aagttcatag | tagggccacc | 9780 |
| aggttccgga | aagaccacct | ggctactgag | tcaagtccag | gacgatgatg | tcatttacac | 9840 |
| acccacccat | cagactatgt | ttgatatagt | cagtgctctc | aaagtttgca | ggtattccat | 9900 |
| tccaggagcc | tcaggactcc | ctttcccacc | acctgccagg | tccggccgt | gggttaggct | 9960 |
| tattgccagc | gggcacgtcc | ctggccgagt | atcatacctc | gatgaggctg | gatattgtaa | 10020 |
| tcatctggac | attcttagac | tgcttttccaa | acacccctt | gtgtgtttgg | gtgaccttca | 10080 |
| gcaacttcac | cctgtcggct | ttgattccta | ctgttatgtg | ttcgatcaga | tgcctcagaa | 10140 |
| gcagctgacc | actatttaca | gatttggccc | taacatctgc | gcagccatcc | agccttgtta | 10200 |
| cagggagaaa | cttgaatcta | aggctaggaa | cactagggtg | gttttacca | cccggcctgt | 10260 |
| ggcctttggt | caggtgctga | caccatacca | taaagatcgc | atcggctctg | cgataaccat | 10320 |
| agattcatcc | caggggggcca | cctttgatat | tgtgacattg | catctaccat | cgccaaagtc | 10380 |
| cctaaataaa | tcccgagcac | ttgtagccat | cactcgggca | agacacgggt | tgttcattta | 10440 |
| tgaccctcat | aaccagctcc | aggagttttt | caacttaacc | cctgagcgca | ctgattgtaa | 10500 |
| ccttgtgttc | agccgtgggg | atgagctggt | agttctgaat | gcggataatg | cagtcacaac | 10560 |
| tgtagcgaag | gcccttgaga | caggtccatc | tcgatttcga | gtatcagacc | cgaggtgcaa | 10620 |
| gtctctctta | gccgcttgtt | cggccagtct | ggaagggagc | tgtatgccac | taccgcaagt | 10680 |
| ggcacataac | ctgggggttttt | acttttcccc | ggacagtcca | acatttgcac | ctctgccaaa | 10740 |
| agagttggcg | ccacattggc | cagtggttac | ccaccagaat | aatcgggcgt | ggcctgatcg | 10800 |
| acttgtcgct | agtatgcgcc | caattgatgc | ccgctacagc | aagccaatgg | tcggtgcagg | 10860 |
| gtatgtggtc | gggccgtcca | ccttttcttgg | tactcctggt | gtggtgtcat | actatctcac | 10920 |
| actatacatc | agggggtgagc | cccaggcctt | gccagaaaca | ctcgtttcaa | cagggcgtat | 10980 |

```
agccacagat tgtcgggagt atctcgacgc ggctgaggaa gaggcagcaa aagaactccc   11040
ccacgcattc attggcgatg tcaaaggtac cacggttggg gggtgtcatc acattacatc   11100
aaaataccta cctaggtccc tgcctaagga ctctgttgcc gtagttggag taagttcgcc   11160
cggcagggct gctaaagccg tgtgcactct caccgatgtg tacctccccg aactccggcc   11220
atatctgcaa cctgagacgg catcaaaatg ctggaaactc aaattagact tcagggacgt   11280
ccgactaatg gtctggaaag gagccaccgc ctatttccag ttggaagggc ttacatggtc   11340
ggcgctgccc gactatgcca ggtttattca gctgcccaag gatgccgttg tatacattga   11400
tccgtgtata ggaccggcaa cagccaaccg taaggtcgtg cgaaccacag actggcgggc   11460
cgacctggca gtgacaccgt atgattacgg tgcccagaac attttgacaa cagcctggtt   11520
cgaggacctc gggccgcagt ggaagatttt ggggttgcag ccctttaggc gagcatttgg   11580 cttttgaaaac actgaggatt gggcaatcct tgcacgccgt atgaatgacg gcaaggacta   11640
cactgactat aactggaact gtgttcgaga acgcccacac gccatctacg ggcgtgctcg   11700
tgaccatacg tatcattttg cccctggcac agaattgcag gtagagctag gtaaaccccg   11760
gctgccgcct gggcaagtgc cgtgaattcg gggtgatgca atggggtcac tgtggagtaa   11820
aatcagccag ctgttcgtgg acgccttcac tgagttcctt gttagtgtgg ttgatattgc   11880
cattttcctt gccatactgt ttgggttcac cgtcgcagga tggttactgg tctttcttct   11940
cagagtggtt tgctccgcgc ttctccgttc gcgctctgcc attcactctc ccgaactatc   12000
gaaggtccta tgaaggcttg ttgcccaact gcagaccgga tgtcccacaa tttgcagtca   12060
agcacccatt gggtatgttt tggcacatgc gagtttccca cttgattgat gagatggtct   12120
ctcgtcgcat ttaccagacc atggaacatt caggtcaagc ggcctggaag caggtggttg   12180
gtgaggccac tctcacgaag ctgtcagggc tcgatatagt tactcatttc caacacctgg   12240
ccgcagtgga ggcggattct tgccgctttc tcagctcacg actcgtgatg ctaaaaaatc   12300
ttgccgttgg caatgtgagc ctacagtaca acaccacgtt ggaccgcgtt gagctcatct   12360
tccccacgcc aggtacgagg cccaagttga ccgatttcag acaatggctc atcagtgtgc   12420
acgcttccat ttttttcctct gtggcttcat ctgttacctt gttcatagtg ctttggcttc   12480
gaattccagc tctacgctat gttttttggtt tccattggcc cacggcaaca catcattcga   12540
gctgaccatc aactacacca tatgcatgcc ctgttctacc agtcaagcgg ctcgccaaag   12600
gctcgagccc ggtcgtaaca tgtggtgcaa aatagggcat gacaggtgtg aggagcgtga   12660
ccatgatgag ttgttaatgt ccatcccgtc cgggtacgac aacctcaaac ttgagggtta   12720
ttatgcttgg ctggcttttt tgtccttttc ctacgcggcc caattccatc cggagttgtt   12780
cgggataggg aatgtgtcgc gcgtcttcgt ggacaagcga caccagttca tttgtgccga   12840
gcatgatgga cacaattcaa ccgtatctac cggacacaac atctccgcat tatatgcggc   12900
atattaccac caccaaatag acgggggcaa ttggttccat ttggaatggc tgcggccact   12960
cttttcttcc tggctggtgc tcaacatatc atggtttctg aggcgttcgc ctgtaagccc   13020
tgtttctcga cgcatctatc agatattgag accaacacga ccgcggctgc cggtttcatg   13080
gtccttcagg acatcaattg tttccgacct cacgggtct cagcagcgca agagaaaatt   13140
tccttcggaa agtcgtccca atgtcgtgaa gccgtcggta ctcccagta catcacgata   13200 acggctaacg tgaccgacga atcatacttg tacaacgcgg acctgctgat gctttctgcg   13260
tgccttttct acgcctcaga aatgagcgag aaaggcttca agtcatcttt gggaatgtc   13320
```

-continued

```
tctggcgttg tttctgcttg tgtcaatttc acagattatg tggcccatgt gacccaacat    13380
acccagcagc atcatctggt aattgatcac attcggttgc tgcatttcct gacaccatct    13440
gcaatgaggt gggctacaac cattgcttgt tgttcgcca ttctcttggc aatatgagat     13500
gttctcacaa attgggcgt tcttgactc cgcactcttg cttctggtgg cttttttgc       13560
tgtgtaccgg cttgtcctgg tcctttgccg atggcaacgg cgacagctcg acataccaat   13620
acatatataa cttgacgata tgcgagctga atggaccga ctggttgtcc agccattttg     13680
gttgggcagt cgagaccttt gtgctttacc cggttgccac tcatatcctc tcactgggtt   13740
ttctcacaac aagccatttt tttgacgcgc tcggtctcgg cgctgtatcc actgcaggat   13800
ttgttggcgg gcggtacgta ctctgcagcg tctacggcgc ttgtgctttc gcagcgttcg   13860
tatgttttgt catccgtgct gctaaaaatt gcatggcctg ccgctatgcc cgtacccggt   13920
ttaccaactt cattgtggac gaccggggga gagttcatcg atggaagtct ccaatagtgg   13980
tagaaaaatt gggcaaagcc gaagtcgatg gcaacctcgt caccatcaaa catgtcgtcc   14040
tcgaagggt taaagctcaa cccttgacga ggacttcggc tgagcaatgg gaggcctaga   14100
cgattttgc aacgatccta cgccgcaca aaagctcgtg ctagccttta gcatcacata    14160
cacacctata atgatatacg cccttaaggt gtcacgcggc cgactcctgg ggctgttgca    14220
catcctaata tttctgaact gttcctttac attcggatac atgacatatg tgcattttca   14280
atccaccaac cgtgtcgcac ttaccctggg ggctgttgtc gcccttctgt ggggtgttta   14340
cagcttcaca gagtcatgga gtttatcac ttccagatgc agattgtgtt gccttggccg    14400
gcgatacatt ctggcccctg cccatcacgt agaaagtgct gcaggtctcc attcaatctc    14460
agcgtctggt aaccgagcat acgctgtgag aaagcccgga ctaacatcag tgaacggcac    14520
tctagtacca ggacttcgga gcctcgtgct gggcggcaaa cgagctgtta aacgaggagt    14580
ggttaacctc gtcaagtatg gccggtaaaa accagagcca gaagaaaaag aaaagtacag    14640
ctccgatggg gaatggccag ccagtcaatc aactgtgcca gttgctgggt gcaatgataa    14700
agtcccagcg ccagcaacct aggggaggac aggccaaaaa gaaaaagcct gagaagccac    14760
atttttcccct ggctgctgaa gatgacatcc ggcaccacct cacccagact gaacgctccc    14820
tctgcttgca atcgatccag acggctttca atcaaggcgc aggaactgcg tcgctttcat    14880
ccagcgggaa ggtcagtttt caggttgagt ttatgctgcc ggttgctcat acagtgcgcc    14940
tgattcgcgt gacttctaca tccgccagtc agggtgcaag ttaatttgac agtcaggtga    15000
atggccgcga ttggcgtgtg gcctctgagt cacctattca attagggcga tcacatgggg    15060
gtcatactta atcaggcagg aaccatgtga ccgaaattaa aaaaaaaaa a              15111
```

<210> SEQ ID NO 5
<211> LENGTH: 33
<212> TYPE: DNA
<213> ORGANISM: Artificial sequence
<220> FEATURE:
<223> OTHER INFORMATION: Synthesized sequence, primer

<400> SEQUENCE: 5
aatcggatcc tcaggaagcg tgcacactga tga                                  33

<210> SEQ ID NO 6
<211> LENGTH: 249
<212> TYPE: PRT
<213> ORGANISM: Lelystad virus

<400> SEQUENCE: 6

-continued

```
Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Pro Phe Ser Leu
            20                  25                  30

Pro Tyr Cys Leu Gly Ser Pro Ser Gln Asp Gly Tyr Trp Ser Phe Phe
        35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Gly Met Phe Trp
                85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

<210> SEQ ID NO 7
<211> LENGTH: 201
<212> TYPE: PRT
<213> ORGANISM: Lelystad virus

<400> SEQUENCE: 7

```
Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
```

```
                115                 120                 125
Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200

<210> SEQ ID NO 8
<211> LENGTH: 3859
<212> TYPE: PRT
<213> ORGANISM: Lelystad virus

<400> SEQUENCE: 8

Met Ser Gly Thr Phe Ser Arg Cys Met Cys Thr Pro Ala Ala Arg Val
1               5                   10                  15

Phe Trp Asn Ala Gly Gln Val Phe Cys Thr Arg Cys Leu Ser Ala Arg
            20                  25                  30

Ser Leu Leu Ser Pro Glu Leu Gln Asp Thr Asp Leu Gly Ala Val Gly
        35                  40                  45

Leu Phe Tyr Lys Pro Arg Asp Lys Leu His Trp Lys Val Pro Ile Gly
    50                  55                  60

Ile Pro Gln Val Glu Cys Thr Pro Ser Gly Cys Cys Trp Leu Ser Ala
65                  70                  75                  80

Val Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Ala
            100                 105                 110

Pro Arg His Leu Arg Glu Leu Gln Val Tyr Glu Arg Gly Cys Asn Trp
        115                 120                 125

Tyr Pro Ile Thr Gly Pro Val Pro Gly Met Gly Leu Phe Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Leu Asn Gly Arg Ser Arg Met Met Trp Thr Pro Glu
        195                 200                 205

Ser Asp Asp Ser Ala Ala Leu Glu Val Leu Pro Pro Glu Leu Glu Arg
    210                 215                 220

Gln Val Glu Ile Leu Ile Arg Ser Phe Pro Ala His His Pro Val Asp
225                 230                 235                 240

Leu Ala Asp Trp Glu Leu Thr Glu Ser Pro Glu Asn Gly Phe Ser Phe
                245                 250                 255

Asn Thr Ser His Ser Cys Gly His Leu Val Gln Asn Pro Asp Val Phe
            260                 265                 270

Asp Gly Lys Cys Trp Leu Ser Cys Phe Leu Gly Gln Ser Val Glu Val
        275                 280                 285
```

```
Arg Cys His Glu Glu His Leu Ala Asp Ala Phe Gly Tyr Gln Thr Lys
290                 295                 300

Trp Gly Val His Gly Lys Tyr Leu Gln Arg Arg Leu Gln Val Arg Gly
305                 310                 315                 320

Ile Arg Ala Val Val Asp Pro Asp Gly Pro Ile His Val Glu Ala Leu
                325                 330                 335

Ser Cys Pro Gln Ser Trp Ile Arg His Leu Thr Leu Asp Asp Asp Val
                340                 345                 350

Thr Pro Gly Phe Val Arg Leu Thr Ser Leu Arg Ile Val Pro Asn Thr
            355                 360                 365

Glu Pro Thr Thr Ser Arg Ile Phe Arg Phe Gly Ala His Lys Trp Tyr
370                 375                 380

Gly Ala Gly Lys Arg Ala Arg Ala Lys Arg Ala Ala Lys Ser Glu
385                 390                 395                 400

Lys Asp Ser Ala Pro Thr Pro Lys Val Ala Leu Pro Val Pro Thr Cys
                405                 410                 415

Gly Ile Thr Thr Tyr Ser Pro Pro Thr Asp Gly Ser Cys Gly Trp His
                420                 425                 430

Val Leu Ala Ala Ile Met Asn Arg Met Ile Asn Gly Asp Phe Thr Ser
            435                 440                 445

Pro Leu Thr Gln Tyr Asn Arg Pro Glu Asp Asp Trp Ala Ser Asp Tyr
450                 455                 460

Asp Leu Val Gln Ala Ile Gln Cys Leu Arg Leu Pro Ala Thr Val Val
465                 470                 475                 480

Arg Asn Arg Ala Cys Pro Asn Ala Lys Tyr Leu Ile Lys Leu Asn Gly
                485                 490                 495

Val His Trp Glu Val Glu Val Arg Ser Gly Met Ala Pro Arg Ser Leu
            500                 505                 510

Ser Arg Glu Cys Val Val Gly Val Cys Ser Glu Gly Cys Val Ala Pro
        515                 520                 525

Pro Tyr Pro Ala Asp Gly Leu Pro Lys Arg Ala Leu Glu Ala Leu Ala
    530                 535                 540

Ser Ala Tyr Arg Leu Pro Ser Asp Cys Val Ser Ser Gly Ile Ala Asp
545                 550                 555                 560

Phe Leu Ala Asn Pro Pro Pro Gln Glu Phe Trp Thr Leu Asp Lys Met
                565                 570                 575

Leu Thr Ser Pro Ser Pro Glu Arg Ser Gly Phe Ser Ser Leu Tyr Lys
            580                 585                 590

Leu Leu Leu Glu Val Val Pro Gln Lys Cys Gly Ala Thr Glu Gly Ala
        595                 600                 605

Phe Ile Tyr Ala Val Glu Arg Met Leu Lys Asp Cys Pro Ser Ser Lys
    610                 615                 620

Gln Ala Met Ala Leu Leu Ala Lys Ile Lys Val Pro Ser Ser Lys Ala
625                 630                 635                 640

Pro Ser Val Ser Leu Asp Glu Cys Phe Pro Thr Asp Val Leu Ala Asp
                645                 650                 655

Phe Glu Pro Ala Ser Gln Glu Arg Pro Gln Ser Ser Gly Ala Ala Val
                660                 665                 670

Val Leu Cys Ser Pro Asp Ala Lys Glu Phe Glu Glu Ala Ala Pro Glu
            675                 680                 685

Glu Val Gln Glu Ser Gly His Lys Ala Val His Ser Ala Leu Leu Ala
690                 695                 700

Glu Gly Pro Asn Asn Glu Gln Val Gln Val Val Ala Gly Glu Gln Leu
```

-continued

```
            705                 710                 715                 720
    Lys Leu Gly Gly Cys Gly Leu Ala Val Gly Asn Ala His Glu Gly Ala
                        725                 730                 735
    Leu Val Ser Ala Gly Leu Ile Asn Leu Val Gly Gly Asn Leu Ser Pro
                740                 745                 750
    Ser Asp Pro Met Lys Glu Asn Met Leu Asn Ser Arg Glu Asp Glu Pro
                755                 760                 765
    Leu Asp Leu Ser Gln Pro Ala Pro Ser Thr Thr Thr Leu Val Arg
                770                 775             780
    Glu Gln Thr Pro Asp Asn Pro Gly Ser Asp Ala Gly Ala Leu Pro Val
    785                 790                 795                 800
    Thr Val Arg Glu Phe Val Pro Thr Gly Pro Ile Leu Cys His Val Glu
                    805                 810                 815
    His Cys Gly Thr Glu Ser Gly Asp Ser Ser Pro Leu Asp Leu Ser
                    820                 825             830
    Asp Ala Gln Thr Leu Asp Gln Pro Leu Asn Leu Ser Leu Ala Ala Trp
                835                 840                 845
    Pro Val Arg Ala Thr Ala Ser Asp Pro Gly Trp Val His Gly Arg Arg
    850                 855                 860
    Glu Pro Val Phe Val Lys Pro Arg Asn Ala Phe Ser Asp Gly Asp Ser
    865                 870                 875                 880
    Ala Leu Gln Phe Gly Glu Leu Ser Glu Ser Ser Val Ile Glu Phe
                    885                 890                 895
    Asp Arg Thr Lys Asp Ala Pro Val Val Asp Ala Pro Val Asp Leu Thr
                900                 905                 910
    Thr Ser Asn Glu Ala Leu Ser Val Val Asp Pro Phe Glu Phe Ala Glu
                915                 920                 925
    Leu Lys Arg Pro Arg Phe Ser Ala Gln Ala Leu Ile Asp Arg Gly Gly
                930                 935                 940
    Pro Leu Ala Asp Val His Ala Lys Ile Lys Asn Arg Val Tyr Glu Gln
    945                 950                 955                 960
    Cys Leu Gln Ala Cys Glu Pro Gly Ser Arg Ala Thr Pro Ala Thr Arg
                    965                 970                 975
    Glu Trp Leu Asp Lys Met Trp Asp Arg Val Asp Met Lys Thr Trp Arg
                980                 985                 990
    Cys Thr Ser Gln Phe Gln Ala Gly  Arg Ile Leu Ala Ser  Leu Lys Phe
                995                 1000                1005
    Leu Pro  Asp Met Ile Gln Asp  Thr Pro Pro Val  Pro Arg Lys
        1010                1015                1020
    Asn Arg  Ala Ser Asp Asn Ala  Gly Leu Lys Gln Leu  Val Ala Gln
        1025                1030                1035
    Trp Asp  Arg Lys Leu Ser Val  Thr Pro Pro Lys  Pro Val Gly
        1040                1045                1050
    Pro Val  Leu Asp Gln Ile Val  Pro Pro Pro Thr Asp  Ile Gln Gln
        1055                1060                1065
    Glu Asp  Val Thr Pro Ser Asp  Gly Pro Pro His Ala  Pro Asp Phe
        1070                1075                1080
    Pro Ser  Arg Val Ser Thr Gly  Gly Ser Trp Lys Gly  Leu Met Leu
        1085                1090                1095
    Ser Gly  Thr Arg Leu Ala Gly  Ser Ile Ser Gln Arg  Leu Met Thr
        1100                1105                1110
    Trp Val  Phe Glu Val Phe Ser  His Leu Pro Ala Phe  Met Leu Thr
        1115                1120                1125
```

-continued

```
Leu Phe Ser Pro Arg Gly Ser Met Ala Pro Gly Asp Trp Leu Phe
    1130                1135                1140

Ala Gly Val Val Leu Leu Ala Leu Leu Leu Cys Arg Ser Tyr Pro
    1145                1150                1155

Ile Leu Gly Cys Leu Pro Leu Leu Gly Val Phe Ser Gly Ser Leu
    1160                1165                1170

Arg Arg Val Arg Leu Gly Val Phe Gly Ser Trp Met Ala Phe Ala
    1175                1180                1185

Val Phe Leu Phe Ser Thr Pro Ser Asn Pro Val Gly Ser Ser Cys
    1190                1195                1200

Asp His Asp Ser Pro Glu Cys His Ala Glu Leu Leu Ala Leu Glu
    1205                1210                1215

Gln Arg Gln Leu Trp Glu Pro Val Arg Gly Leu Val Val Gly Pro
    1220                1225                1230

Ser Gly Leu Leu Cys Val Ile Leu Gly Lys Leu Leu Gly Gly Ser
    1235                1240                1245

Arg Tyr Leu Trp His Val Leu Leu Arg Leu Cys Met Leu Ala Asp
    1250                1255                1260

Leu Ala Leu Ser Leu Val Tyr Val Val Ser Gln Gly Arg Cys His
    1265                1270                1275

Lys Cys Trp Gly Lys Cys Ile Arg Thr Ala Pro Ala Glu Val Ala
    1280                1285                1290

Leu Asn Val Phe Pro Phe Ser Arg Ala Thr Arg Val Ser Leu Val
    1295                1300                1305

Ser Leu Cys Asp Arg Phe Gln Thr Pro Lys Gly Val Asp Pro Val
    1310                1315                1320

His Leu Ala Thr Gly Trp Arg Gly Cys Trp Arg Gly Glu Ser Pro
    1325                1330                1335

Ile His Gln Pro His Gln Lys Pro Ile Ala Tyr Ala Asn Leu Asp
    1340                1345                1350

Glu Lys Lys Met Ser Ala Gln Thr Val Val Ala Val Pro Tyr Asp
    1355                1360                1365

Pro Ser Gln Ala Ile Lys Cys Leu Lys Val Leu Gln Ala Gly Gly
    1370                1375                1380

Ala Ile Val Asp Gln Pro Thr Pro Glu Val Val Arg Val Ser Glu
    1385                1390                1395

Ile Pro Phe Ser Ala Pro Phe Pro Lys Val Pro Val Asn Pro
    1400                1405                1410

Asp Cys Arg Val Val Val Asp Ser Asp Thr Phe Val Ala Ala Val
    1415                1420                1425

Arg Cys Gly Tyr Ser Thr Ala Gln Leu Val Leu Gly Arg Gly Asn
    1430                1435                1440

Phe Ala Lys Leu Asn Gln Thr Pro Pro Arg Asn Ser Ile Ser Thr
    1445                1450                1455

Lys Thr Thr Gly Gly Ala Ser Tyr Thr Leu Ala Val Ala Gln Val
    1460                1465                1470

Ser Ala Trp Thr Leu Val His Phe Ile Leu Gly Leu Trp Phe Thr
    1475                1480                1485

Ser Pro Gln Val Cys Gly Arg Gly Thr Ala Asp Pro Trp Cys Ser
    1490                1495                1500

Asn Pro Phe Ser Tyr Pro Thr Tyr Gly Pro Gly Val Val Cys Ser
    1505                1510                1515
```

-continued

| | | | | | | | | | | |
|---|---|---|---|---|---|---|---|---|---|---|
| Ser | Arg | Leu | Cys | Val | Ser | Ala | Asp | Gly | Val | Thr | Leu | Pro | Leu | Phe |
| | 1520 | | | | 1525 | | | | 1530 | |

Ser Arg Leu Cys Val Ser Ala Asp Gly Val Thr Leu Pro Leu Phe
     1520                1525              1530

Ser Ala Val Ala Gln Leu Ser Gly Arg Glu Val Gly Ile Phe Ile
     1535                1540              1545

Leu Val Leu Val Ser Leu Thr Ala Leu Ala His Arg Met Ala Leu
     1550                1555              1560

Lys Ala Asp Met Leu Val Val Phe Ser Ala Phe Cys Ala Tyr Ala
     1565                1570              1575

Trp Pro Met Ser Ser Trp Leu Ile Cys Phe Phe Pro Ile Leu Leu
     1580                1585              1590

Lys Trp Val Thr Leu His Pro Leu Thr Met Leu Trp Val His Ser
     1595                1600              1605

Phe Leu Val Phe Cys Leu Pro Ala Ala Gly Ile Leu Ser Leu Gly
     1610                1615              1620

Ile Thr Gly Leu Leu Trp Ala Ile Gly Arg Phe Thr Gln Val Ala
     1625                1630              1635

Gly Ile Ile Thr Pro Tyr Asp Ile His Gln Tyr Thr Ser Gly Pro
     1640                1645              1650

Arg Gly Ala Ala Ala Val Ala Thr Ala Pro Glu Gly Thr Tyr Met
     1655                1660              1665

Ala Ala Val Arg Arg Ala Ala Leu Thr Gly Arg Thr Leu Ile Phe
     1670                1675              1680

Thr Pro Ser Ala Val Gly Ser Leu Leu Glu Gly Ala Phe Arg Thr
     1685                1690              1695

His Lys Pro Cys Leu Asn Thr Val Asn Val Val Gly Ser Ser Leu
     1700                1705              1710

Gly Ser Gly Gly Val Phe Thr Ile Asp Gly Arg Arg Thr Val Val
     1715                1720              1725

Thr Ala Ala His Val Leu Asn Gly Asp Thr Ala Arg Val Thr Gly
     1730                1735              1740

Asp Ser Tyr Asn Arg Met His Thr Phe Lys Thr Asn Gly Asp Tyr
     1745                1750              1755

Ala Trp Ser His Ala Asp Asp Trp Gln Gly Val Ala Pro Val Val
     1760                1765              1770

Lys Val Ala Lys Gly Tyr Arg Gly Arg Ala Tyr Trp Gln Thr Ser
     1775                1780              1785

Thr Gly Val Glu Pro Gly Ile Ile Gly Glu Gly Phe Ala Phe Cys
     1790                1795              1800

Phe Thr Asn Cys Gly Asp Ser Gly Ser Pro Val Ile Ser Glu Ser
     1805                1810              1815

Gly Asp Leu Ile Gly Ile His Thr Gly Ser Asn Lys Leu Gly Ser
     1820                1825              1830

Gly Leu Val Thr Thr Pro Glu Gly Glu Thr Cys Thr Ile Lys Glu
     1835                1840              1845

Thr Lys Leu Ser Asp Leu Ser Arg His Phe Ala Gly Pro Ser Val
     1850                1855              1860

Pro Leu Gly Asp Ile Lys Leu Ser Pro Ala Ile Ile Pro Asp Val
     1865                1870              1875

Thr Ser Ile Pro Ser Asp Leu Ala Ser Leu Leu Ala Ser Val Pro
     1880                1885              1890

Val Val Glu Gly Gly Leu Ser Thr Val Gln Leu Leu Cys Val Phe
     1895                1900              1905

Phe Leu Leu Trp Arg Met Met Gly His Ala Trp Thr Pro Ile Val

-continued

|  |  |  |  |  |  |  |  |  |  |
|---|---|---|---|---|---|---|---|---|---|
| | 1910 | | | | 1915 | | | | 1920 |
| Ala | Val | Gly | Phe | Phe | Leu | Leu | Asn | Glu | Ile | Leu | Pro | Ala | Val | Leu |
| | 1925 | | | | 1930 | | | | 1935 |
| Val | Arg | Ala | Val | Phe | Ser | Phe | Ala | Leu | Phe | Val | Leu | Ala | Trp | Ala |
| | 1940 | | | | 1945 | | | | 1950 |
| Thr | Pro | Trp | Ser | Ala | Gln | Val | Leu | Met | Ile | Arg | Leu | Leu | Thr | Ala |
| | 1955 | | | | 1960 | | | | 1965 |
| Ser | Leu | Asn | Arg | Asn | Lys | Leu | Ser | Leu | Ala | Phe | Tyr | Ala | Leu | Gly |
| | 1970 | | | | 1975 | | | | 1980 |
| Gly | Val | Val | Gly | Leu | Ala | Ala | Glu | Ile | Gly | Thr | Phe | Ala | Gly | Arg |
| | 1985 | | | | 1990 | | | | 1995 |
| Leu | Ser | Glu | Leu | Ser | Gln | Ala | Leu | Ser | Thr | Tyr | Cys | Phe | Leu | Pro |
| | 2000 | | | | 2005 | | | | 2010 |
| Arg | Val | Leu | Ala | Met | Thr | Ser | Cys | Val | Pro | Thr | Ile | Ile | Ile | Gly |
| | 2015 | | | | 2020 | | | | 2025 |
| Gly | Leu | His | Thr | Leu | Gly | Val | Ile | Leu | Trp | Leu | Phe | Lys | Tyr | Arg |
| | 2030 | | | | 2035 | | | | 2040 |
| Cys | Leu | His | Asn | Met | Leu | Val | Gly | Asp | Gly | Ser | Phe | Ser | Ser | Ala |
| | 2045 | | | | 2050 | | | | 2055 |
| Phe | Phe | Leu | Arg | Tyr | Phe | Ala | Glu | Gly | Asn | Leu | Arg | Lys | Gly | Val |
| | 2060 | | | | 2065 | | | | 2070 |
| Ser | Gln | Ser | Cys | Gly | Met | Asn | Asn | Glu | Ser | Leu | Thr | Ala | Ala | Leu |
| | 2075 | | | | 2080 | | | | 2085 |
| Ala | Cys | Lys | Leu | Ser | Gln | Ala | Asp | Leu | Asp | Phe | Leu | Ser | Ser | Leu |
| | 2090 | | | | 2095 | | | | 2100 |
| Thr | Asn | Phe | Lys | Cys | Phe | Val | Ser | Ala | Ser | Asn | Met | Lys | Asn | Ala |
| | 2105 | | | | 2110 | | | | 2115 |
| Ala | Gly | Gln | Tyr | Ile | Glu | Ala | Ala | Tyr | Ala | Lys | Ala | Leu | Arg | Gln |
| | 2120 | | | | 2125 | | | | 2130 |
| Glu | Leu | Ala | Ser | Leu | Val | Gln | Ile | Asp | Lys | Met | Lys | Gly | Val | Leu |
| | 2135 | | | | 2140 | | | | 2145 |
| Ser | Lys | Leu | Glu | Ala | Phe | Ala | Glu | Thr | Ala | Thr | Pro | Ser | Leu | Asp |
| | 2150 | | | | 2155 | | | | 2160 |
| Ile | Gly | Asp | Val | Ile | Val | Leu | Leu | Gly | Gln | His | Pro | His | Gly | Ser |
| | 2165 | | | | 2170 | | | | 2175 |
| Ile | Leu | Asp | Ile | Asn | Val | Gly | Thr | Glu | Arg | Lys | Thr | Val | Ser | Val |
| | 2180 | | | | 2185 | | | | 2190 |
| Gln | Glu | Thr | Arg | Ser | Leu | Gly | Gly | Ser | Lys | Phe | Ser | Val | Cys | Thr |
| | 2195 | | | | 2200 | | | | 2205 |
| Val | Val | Ser | Asn | Thr | Pro | Val | Asp | Ala | Leu | Thr | Gly | Ile | Pro | Leu |
| | 2210 | | | | 2215 | | | | 2220 |
| Gln | Thr | Pro | Thr | Pro | Leu | Phe | Glu | Asn | Gly | Pro | Arg | His | Arg | Ser |
| | 2225 | | | | 2230 | | | | 2235 |
| Glu | Glu | Asp | Asp | Leu | Lys | Val | Glu | Arg | Met | Lys | Lys | His | Cys | Val |
| | 2240 | | | | 2245 | | | | 2250 |
| Ser | Leu | Gly | Phe | His | Asn | Ile | Asn | Gly | Lys | Val | Tyr | Cys | Lys | Ile |
| | 2255 | | | | 2260 | | | | 2265 |
| Trp | Asp | Lys | Ser | Thr | Gly | Asp | Thr | Phe | Tyr | Thr | Asp | Asp | Ser | Arg |
| | 2270 | | | | 2275 | | | | 2280 |
| Tyr | Thr | Gln | Asp | His | Ala | Phe | Gln | Asp | Arg | Ser | Ala | Asp | Tyr | Arg |
| | 2285 | | | | 2290 | | | | 2295 |
| Asp | Arg | Asp | Tyr | Glu | Gly | Val | Gln | Thr | Thr | Pro | Gln | Gln | Gly | Phe |
| | 2300 | | | | 2305 | | | | 2310 |

-continued

```
Asp Pro Lys Ser Glu Thr Pro Val Gly Thr Val Val Ile Gly Gly
    2315                2320                2325
Ile Thr Tyr Asn Arg Tyr Leu Ile Lys Gly Lys Glu Val Leu Val
    2330                2335                2340
Pro Lys Pro Asp Asn Cys Leu Glu Ala Ala Lys Leu Ser Leu Glu
    2345                2350                2355
Gln Ala Leu Ala Gly Met Gly Gln Thr Cys Asp Leu Thr Ala Ala
    2360                2365                2370
Glu Val Glu Lys Leu Lys Arg Ile Ile Ser Gln Leu Gln Gly Leu
    2375                2380                2385
Thr Thr Glu Gln Ala Leu Asn Cys Thr Gly Phe Lys Leu Leu Ala
    2390                2395                2400
Ala Ser Gly Leu Thr Arg Cys Gly Arg Gly Leu Val Val Thr
    2405                2410                2415
Glu Thr Ala Val Lys Ile Ile Lys Tyr His Ser Arg Thr Phe Thr
    2420                2425                2430
Leu Gly Pro Leu Asp Leu Lys Val Thr Ser Glu Val Glu Val Lys
    2435                2440                2445
Lys Ser Thr Glu Gln Gly His Ala Val Val Ala Asn Leu Cys Ser
    2450                2455                2460
Gly Val Ile Leu Met Arg Pro His Pro Pro Ser Leu Val Asp Val
    2465                2470                2475
Leu Leu Lys Pro Gly Leu Asp Thr Ile Pro Gly Ile Gln Pro Gly
    2480                2485                2490
His Gly Ala Gly Asn Met Gly Val Asp Gly Ser Ile Trp Asp Phe
    2495                2500                2505
Glu Thr Ala Pro Thr Lys Ala Glu Leu Glu Leu Ser Lys Gln Ile
    2510                2515                2520
Ile Gln Ala Cys Glu Val Arg Arg Gly Asp Ala Pro Asn Leu Gln
    2525                2530                2535
Leu Pro Tyr Lys Leu Tyr Pro Val Arg Gly Asp Pro Glu Arg His
    2540                2545                2550
Lys Gly Arg Leu Ile Asn Thr Arg Phe Gly Asp Leu Pro Tyr Lys
    2555                2560                2565
Thr Pro Gln Asp Thr Lys Ser Ala Ile His Ala Ala Cys Cys Leu
    2570                2575                2580
His Pro Asn Gly Ala Pro Val Ser Asp Gly Lys Ser Thr Leu Gly
    2585                2590                2595
Thr Thr Leu Gln His Gly Phe Glu Leu Tyr Val Pro Thr Val Pro
    2600                2605                2610
Tyr Ser Val Met Glu Tyr Leu Asp Ser Arg Pro Asp Thr Pro Phe
    2615                2620                2625
Met Cys Thr Lys His Gly Thr Ser Lys Ala Ala Ala Glu Asp Leu
    2630                2635                2640
Gln Lys Tyr Asp Leu Ser Thr Gln Gly Phe Val Leu Pro Gly Val
    2645                2650                2655
Leu Arg Leu Val Arg Arg Phe Ile Phe Gly His Ile Gly Lys Ala
    2660                2665                2670
Pro Pro Leu Phe Leu Pro Ser Thr Tyr Pro Ala Lys Asn Ser Met
    2675                2680                2685
Ala Gly Ile Asn Gly Gln Arg Phe Pro Thr Lys Asp Val Gln Ser
    2690                2695                2700
```

```
Ile Pro Glu Ile Asp Glu Met Cys Ala Arg Ala Val Lys Glu Asn
2705             2710                 2715

Trp Gln Thr Val Thr Pro Cys Thr Leu Lys Lys Gln Tyr Cys Ser
2720             2725                 2730

Lys Pro Lys Thr Arg Thr Ile Leu Gly Thr Asn Asn Phe Ile Ala
2735             2740                 2745

Leu Ala His Arg Ser Ala Leu Ser Gly Val Thr Gln Ala Phe Met
2750             2755                 2760

Lys Lys Ala Trp Lys Ser Pro Ile Ala Leu Gly Lys Asn Lys Phe
2765             2770                 2775

Lys Glu Leu His Cys Thr Val Ala Gly Arg Cys Leu Glu Ala Asp
2780             2785                 2790

Leu Ala Ser Cys Asp Arg Ser Thr Pro Ala Ile Val Arg Trp Phe
2795             2800                 2805

Val Ala Asn Leu Leu Tyr Glu Leu Ala Gly Cys Glu Glu Tyr Leu
2810             2815                 2820

Pro Ser Tyr Val Leu Asn Cys Cys His Asp Leu Val Ala Thr Gln
2825             2830                 2835

Asp Gly Ala Phe Thr Lys Arg Gly Gly Leu Ser Ser Gly Asp Pro
2840             2845                 2850

Val Thr Ser Val Ser Asn Thr Val Tyr Ser Leu Val Ile Tyr Ala
2855             2860                 2865

Gln His Met Val Leu Ser Ala Leu Lys Met Gly His Glu Ile Gly
2870             2875                 2880

Leu Lys Phe Leu Glu Glu Gln Leu Lys Phe Glu Asp Leu Leu Glu
2885             2890                 2895

Ile Gln Pro Met Leu Val Tyr Ser Asp Asp Leu Val Leu Tyr Ala
2900             2905                 2910

Glu Arg Pro Thr Phe Pro Asn Tyr His Trp Trp Val Glu His Leu
2915             2920                 2925

Asp Leu Met Leu Gly Phe Arg Thr Asp Pro Lys Lys Thr Val Ile
2930             2935                 2940

Thr Asp Lys Pro Ser Phe Leu Gly Cys Arg Ile Glu Ala Gly Arg
2945             2950                 2955

Gln Leu Val Pro Asn Arg Asp Arg Ile Leu Ala Ala Leu Ala Tyr
2960             2965                 2970

His Met Lys Ala Gln Asn Ala Ser Glu Tyr Tyr Ala Ser Ala Ala
2975             2980                 2985

Ala Ile Leu Met Asp Ser Cys Ala Cys Ile Asp His Asp Pro Glu
2990             2995                 3000

Trp Tyr Glu Asp Leu Ile Cys Gly Ile Ala Arg Cys Ala Arg Gln
3005             3010                 3015

Asp Gly Tyr Ser Phe Pro Gly Pro Ala Phe Phe Met Ser Met Trp
3020             3025                 3030

Glu Lys Leu Arg Ser His Asn Glu Gly Lys Lys Phe Arg His Cys
3035             3040                 3045

Gly Ile Cys Asp Ala Lys Ala Asp Tyr Ala Ser Ala Cys Gly Leu
3050             3055                 3060

Asp Leu Cys Leu Phe His Ser His Phe His Gln His Cys Pro Val
3065             3070                 3075

Thr Leu Ser Cys Gly His His Ala Gly Ser Lys Glu Cys Ser Gln
3080             3085                 3090

Cys Gln Ser Pro Val Gly Ala Gly Arg Ser Pro Leu Asp Ala Val
```

|     |     |     |     |     |     |     |     |     |     |
|-----|-----|-----|-----|-----|-----|-----|-----|-----|-----|
|     |     |     |     | 3095 |     |     | 3100 |     | 3105 |
| Leu | Lys | Gln | Ile | Pro | Tyr | Lys | Pro | Pro | Arg | Thr | Val | Ile | Met | Lys |

Leu Lys Gln Ile Pro Tyr Lys Pro Pro Arg Thr Val Ile Met Lys
          3110                    3115                    3120

Val Gly Asn Lys Thr Thr Ala Leu Asp Pro Gly Arg Tyr Gln Ser
          3125                    3130                    3135

Arg Arg Gly Leu Val Ala Val Lys Arg Gly Ile Ala Gly Asn Glu
          3140                    3145                    3150

Val Asp Leu Ser Asp Gly Asp Tyr Gln Val Val Pro Leu Leu Pro
          3155                    3160                    3165

Thr Cys Lys Asp Ile Asn Met Val Lys Val Ala Cys Asn Val Leu
          3170                    3175                    3180

Leu Ser Lys Phe Ile Val Gly Pro Pro Gly Ser Gly Lys Thr Thr
          3185                    3190                    3195

Trp Leu Leu Ser Gln Val Gln Asp Asp Val Ile Tyr Thr Pro
          3200                    3205                    3210

Thr His Gln Thr Met Phe Asp Ile Val Ser Ala Leu Lys Val Cys
          3215                    3220                    3225

Arg Tyr Ser Ile Pro Gly Ala Ser Gly Leu Pro Phe Pro Pro Pro
          3230                    3235                    3240

Ala Arg Ser Gly Pro Trp Val Arg Leu Ile Ala Ser Gly His Val
          3245                    3250                    3255

Pro Gly Arg Val Ser Tyr Leu Asp Glu Ala Gly Tyr Cys Asn His
          3260                    3265                    3270

Leu Asp Ile Leu Arg Leu Leu Ser Lys Thr Pro Leu Val Cys Leu
          3275                    3280                    3285

Gly Asp Leu Gln Gln Leu His Pro Val Gly Phe Asp Ser Tyr Cys
          3290                    3295                    3300

Tyr Val Phe Asp Gln Met Pro Gln Lys Gln Leu Thr Thr Ile Tyr
          3305                    3310                    3315

Arg Phe Gly Pro Asn Ile Cys Ala Ala Ile Gln Pro Cys Tyr Arg
          3320                    3325                    3330

Glu Lys Leu Glu Ser Lys Ala Arg Asn Thr Arg Val Val Phe Thr
          3335                    3340                    3345

Thr Arg Pro Val Ala Phe Gly Gln Val Leu Thr Pro Tyr His Lys
          3350                    3355                    3360

Asp Arg Ile Gly Ser Ala Ile Thr Ile Asp Ser Ser Gln Gly Ala
          3365                    3370                    3375

Thr Phe Asp Ile Val Thr Leu His Leu Pro Ser Pro Lys Ser Leu
          3380                    3385                    3390

Asn Lys Ser Arg Ala Leu Val Ala Ile Thr Arg Ala Arg His Gly
          3395                    3400                    3405

Leu Phe Ile Tyr Asp Pro His Asn Gln Leu Gln Glu Phe Phe Asn
          3410                    3415                    3420

Leu Thr Pro Glu Arg Thr Asp Cys Asn Leu Val Phe Ser Arg Gly
          3425                    3430                    3435

Asp Glu Leu Val Val Leu Asn Ala Asp Asn Ala Val Thr Thr Val
          3440                    3445                    3450

Ala Lys Ala Leu Glu Thr Gly Pro Ser Arg Phe Arg Val Ser Asp
          3455                    3460                    3465

Pro Arg Cys Lys Ser Leu Leu Ala Ala Cys Ser Ala Ser Leu Glu
          3470                    3475                    3480

Gly Ser Cys Met Pro Leu Pro Gln Val Ala His Asn Leu Gly Phe
          3485                    3490                    3495

-continued

```
Tyr Phe Ser Pro Asp Ser Pro Thr Phe Ala Pro Leu Pro Lys Glu
    3500            3505                3510

Leu Ala Pro His Trp Pro Val Val Thr His Gln Asn Asn Arg Ala
    3515            3520                3525

Trp Pro Asp Arg Leu Val Ala Ser Met Arg Pro Ile Asp Ala Arg
    3530            3535                3540

Tyr Ser Lys Pro Met Val Gly Ala Gly Tyr Val Val Gly Pro Ser
    3545            3550                3555

Thr Phe Leu Gly Thr Pro Gly Val Val Ser Tyr Tyr Leu Thr Leu
    3560            3565                3570

Tyr Ile Arg Gly Glu Pro Gln Ala Leu Pro Glu Thr Leu Val Ser
    3575            3580                3585

Thr Gly Arg Ile Ala Thr Asp Cys Arg Glu Tyr Leu Asp Ala Ala
    3590            3595                3600

Glu Glu Glu Ala Ala Lys Glu Leu Pro His Ala Phe Ile Gly Asp
    3605            3610                3615

Val Lys Gly Thr Thr Val Gly Gly Cys His His Ile Thr Ser Lys
    3620            3625                3630

Tyr Leu Pro Arg Ser Leu Pro Lys Asp Ser Val Ala Val Val Gly
    3635            3640                3645

Val Ser Ser Pro Gly Arg Ala Ala Lys Ala Val Cys Thr Leu Thr
    3650            3655                3660

Asp Val Tyr Leu Pro Glu Leu Arg Pro Tyr Leu Gln Pro Glu Thr
    3665            3670                3675

Ala Ser Lys Cys Trp Lys Leu Lys Leu Asp Phe Arg Asp Val Arg
    3680            3685                3690

Leu Met Val Trp Lys Gly Ala Thr Ala Tyr Phe Gln Leu Glu Gly
    3695            3700                3705

Leu Thr Trp Ser Ala Leu Pro Asp Tyr Ala Arg Phe Ile Gln Leu
    3710            3715                3720

Pro Lys Asp Ala Val Val Tyr Ile Asp Pro Cys Ile Gly Pro Ala
    3725            3730                3735

Thr Ala Asn Arg Lys Val Val Arg Thr Thr Asp Trp Arg Ala Asp
    3740            3745                3750

Leu Ala Val Thr Pro Tyr Asp Tyr Gly Ala Gln Asn Ile Leu Thr
    3755            3760                3765

Thr Ala Trp Phe Glu Asp Leu Gly Pro Gln Trp Lys Ile Leu Gly
    3770            3775                3780

Leu Gln Pro Phe Arg Arg Ala Phe Gly Phe Glu Asn Thr Glu Asp
    3785            3790                3795

Trp Ala Ile Leu Ala Arg Arg Met Asn Asp Gly Lys Asp Tyr Thr
    3800            3805                3810

Asp Tyr Asn Trp Asn Cys Val Arg Glu Arg Pro His Ala Ile Tyr
    3815            3820                3825

Gly Arg Ala Arg Asp His Thr Tyr His Phe Ala Pro Gly Thr Glu
    3830            3835                3840

Leu Gln Val Glu Leu Gly Lys Pro Arg Leu Pro Pro Gly Gln Val
    3845            3850                3855

Pro
```

ADAPTATION SITES OF PORCINE REPRODUCTIVE AND RESPIRATORY SYNDROME VIRUS

TECHNICAL FIELD

The invention relates to the field of virology and more particularly, to the field of vaccine production. More specifically, the invention relates to the in vitro propagation of virus and to the adaptation of a virus to a cell line and the attenuation of a virus.

BACKGROUND

Porcine reproductive and respiratory syndrome virus (PRRSV) is a small, enveloped, positive-stranded RNA virus which belongs to the genus arterivirus. PRRSV was isolated in Europe and in the United States of America in 1991 (Collins et al., 1992, Wensvoort et al., 1991). The genus arterivirus also includes equine arteritis virus (EAV), lactate dehydrogenase-elevating virus (LDV) and simian hemorrhagic fever virus (SHFV). The genus arterivirus is the only member in the family of the Arteriviridae. The family Arteriviridae and the Coronaviridae are grouped into the order Nidovirales.

In vivo, PRRSV reproduces primarily in porcine alveolar lung macrophages and blood monocytes. (Wensvoort et al., 1991). Macrophages from other tissues, such as heart, tonsil, spleen, turbinates and choroid plexus are also susceptible to PRRSV infection.

In vitro, the porcine virus can be passaged to primary cultures of porcine alveolar lung macrophages and blood monocytes, to cultures of the African green monkey kidney cell line MA-104 and to the derivative cell lines CL2621 and MARC-145. (Collins et al., 1992, Wensvoort et al., 1991). A few cell lines exist that the porcine virus cannot penetrate, such as BHK-21 and Vero cells, but once the genome of these cell lines is brought inside the cells artificially, the porcine virus is able to replicate and produce new virus particles. (Meulenberg et al., 1998).

PRRSV enters porcine alveolar macrophages and MARC-145 cells via receptor-mediated endocytosis. The uptake of PRRSV by the host cell is a multi-step process in which one or two viral constituents appear to interact with at least one host proteonic factor before virus-containing clathrin-coated pits are formed. (Kreutz, 1998). The entry process of PRRSV into porcine macrophages differs from the binding and internalization of PRRSV into MARC-145 cells. A membrane protein of about 210-kDa has been identified as being a putative receptor for PRRSV on macrophages (Duan et al., 1998) while a heparin-like molecule is suggested to be important for the binding of PRRSV to MARC-145 cells. (Jusa et al., 1997).

PRRSV has a concise genome structure (for a review, see, Snijder, and Meulenberg, 1998) which is 15,098 nt in length without the poly-A tail and contains 9 open reading frames (ORFs) flanked by a 5' and 3' non-translated region (NTR) of 221 and 114 nucleotides, respectively. The two 5'-terminal ORFs designated 1A and 1B (FIGS. 1A and 1B) comprise about 75% of the genomic RNA. The structural region of the RNA contains 7 ORFs designated 2A, 2B, and 3 to 7 (FIGS. 1A and 1B) and occupies the 3'-terminal third of the genome. ORF 1A/B encodes the non-structural proteins (nsps) involved in replication of the RNA genome and the forming of a 3' nested set of subgenomic RNAs (sgRNAs).

The first two N-terminal proteins named nsp 1α and nsp 1β, respectively, have been studied for PRRSV. The functions of the other nsps are based on predictions derived from sequence homologies with EAV. Nsp 1α and nsp 1β are papain-like cysteine proteases and together with nsp2 and nsp4, a cysteine protease and a serine protease, respectively, the entire polyprotein ORF1 (a/ab) is assumed to be cleaved into 12 nsps. Nsp9 and 10 are predicted to be the replicase subunits.

The 3'-terminal end of the genome encodes the structural proteins. The ORFs 2A to 6 encode six structural membrane-associated proteins and the most 3'-terminal ORF encodes the N protein (ORF7). The minor glycoproteins are GP2a (formerly named GP2), GP3 and GP4. The GP2a and the GP4 proteins are class I membrane proteins and have molecular masses of 27-30 and 31-35 kDa, respectively. Both N-glycosylated proteins are constituents of the virion. The other minor N-glycosylated structural protein of 42-50 kDa is GP3 and is encoded by ORF3. The nature of GP3 was unclear until the present disclosure.

The three major structural proteins are GP5, M and the N protein. GP5, a N-glycosylated protein of 24-26 kDa, is the most variable protein in its sequence. The most conserved protein is the non-glycosylated M protein. The M protein is a 18-19 kDa integral membrane protein and appears to have a function in viral infectivity. The M protein forms a heterodimer with GP5 which is present in the virion. The N protein is a small, highly basic, nucleocapsid protein of 14-15 kDa which interacts with the viral RNA during assembly. (Snijder & Meulenberg, 1998).

Sequence comparisons and studies involving the antigenic nature of PRRSV strains reveal two distinct groups designated as EU (European) and US (North American) strains. (Wensvoort et al., 1992, Snijder & Meulenberg, 1998). Another indication of the observed diversity between the EU strain and the US strain from the two continents is the fact that EU field isolates initially replicate easier in alveolar lung macrophages, whereas US isolates are recovered easier in the African green monkey kidney cell line MA-104 or derivatives thereof, such as CL2621 or MARC-145 cells. (Bautista et al., 1993).

The candidate proteins which will adsorb to the host cell surface of permissive cells are GP2a, GP2b, GP3, GP4, GP5, the M protein or a heterodimer of GP5 and the M protein.

Typically, when viruses are replicated in vitro in cell lines derived from a different species, the viruses tend to attenuate in the process of adapting to the cell line. This adaptation characteristic is widely used in vaccine development and is also true for PRRSV replicated in monkey cell lines (Collins et al. 1992).

SUMMARY OF THE INVENTION

In one embodiment, changes in the PRRSV genome that occur during the adaptation process are related to adaptation to a cell. This aspect is useful because the PRRSV can be adapted to replicate in a permissive cell without further loss of virulence.

In another embodiment, changes in other sites of the genome are more related to attenuation. This aspect is useful because it enables a person skilled in the art to control the level of attenuation of a PRRSV.

A method to determine the capability of an arterivirus to replicate in a permissive cell, such as a green monkey cell, comprising determining the amino acid positions that correspond to the amino acid positions 75-107 of GP2a of PRRSV isolate I-1102 is disclosed. In a further aspect of the present invention, a method for determining the amino acid positions that correspond to the amino acid position 88 and/or amino acid position 95 of GP2a of PRRSV isolate I-1102 is disclosed. The knowledge and methods disclosed herein will enable a person of ordinary skill in the art to identify the capability of a PRRS virus to replicate in a permissive cell, such as a green monkey cell.

Further, a method for increasing the capability of an arterivirus to replicate in a permissive cell, such as a green monkey cell, comprising changing the amino acids at amino acid positions 75-107 is disclosed. In another aspect, the method comprises changing the amino acid at amino acid position 88 from a valine to any other amino acid, such as a phenylalanine, and/or changing the amino acid at amino acid position 95 from a phenylalanine to any other amino acid, such as a leucine is disclosed.

In a further embodiment, the concomitant amino acid changes in the two sites of GP2a enhance the adaptation of a PRRSV for a permissive cell, such as a green monkey cell. The method is suited for the production of an arterivirus and/or a nucleic acid in a permissive cell and/or cell line, wherein the virulence of the arterivirus is maintained while the virus and/or nucleic acid yield from the permissive cell and/or cell line is increased.

In another embodiment, a method for determining the attenuation of an Arterivirus comprising determining the amino acids positions that correspond to the amino acid positions 121-148 of GP5 of PRRSV isolate I-1102 is disclosed. The method further comprises determining the amino acid position that corresponds to the amino acid position 136 of GP5 of PRRSV isolate I-1102. A method to control and/or increase the attenuation of an arterivirus comprising changing amino acids at amino acid positions 121-148 of GP5 of PRRSV isolate I-1102 by changing the amino acid at amino acid position 136 from a cysteine to any other amino acid, such as a tyrosine, is disclosed.

In a further embodiment, a method for determining the attenuation of an Arterivirus comprising determining the amino acids at positions that correspond to the amino acid positions 651-675 and/or amino acid positions 2331-2355 of ORFlab of PRRSV isolate I-1102 is disclosed. The method further comprises determining the amino acid at a position that corresponds to the amino acid position 663 and/or amino acid position 2343 of ORFlab of PRRSV isolate I-1102. A method to control and/or increase the attenuation of an arterivirus comprising changing amino acids at amino acid positions 121-148 of GP5 of PRRSV isolate I-1102 by changing the amino acid at amino acid position 136 from a cysteine to any other amino acid, such as a tyrosine, is disclosed.

In another embodiment, a method for determining the attenuation of an Arterivirus comprising determining the amino acids positions that correspond to the amino acid positions 651-675 and/or amino acid positions 2331-2355 of ORFlab of PRRSV isolate I-1102 is disclosed. In a further aspect, the method comprises determining the amino acid at positions that corresponds to the amino acid position 663 and/or amino acid position 2343 of ORFlab of PRRSV isolate I-1102.

A method to control and/or increase the attenuation of an arterivirus comprising changing the amino acids at positions that correspond to the amino acid positions 651-675 and/or amino acid positions 2331-2355 of ORFlab of PRRSV isolate I-1102 is disclosed. In a further aspect, the method comprises changing the amino acid at amino acid position 663 from a glutamic acid to any other amino acid, such a lysine, and/or changing the amino acid at amino acid position 2343 from a valine to any other amino acid, such as an alanine. The methods also allow for the production of an attenuated arterivirus.

BRIEF DESCRIPTION OF THE DRAWINGS

FIG. 2A: Multi-step growth curves on MARC-145 cells. Virus titer is in TDID50/ml.

FIG. 2B: Multi-step growth curves on PAMs. Virus titer is in TCID50/ml.

DETAILED DESCRIPTION

Figure 1A:
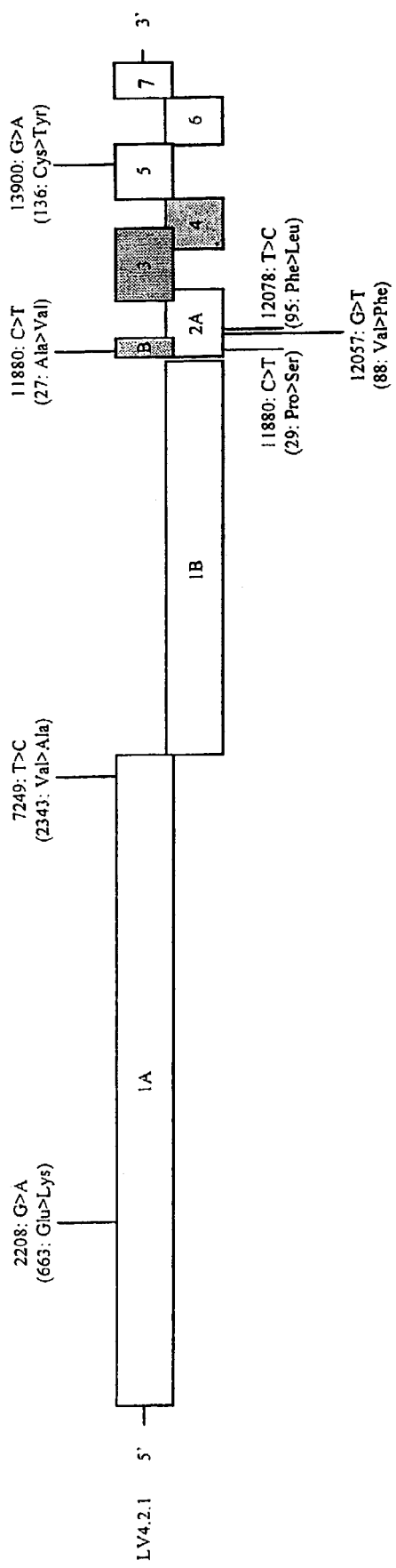
FIGS. 1A and 1B: Schematic representation of amino acid differences between the LV4.2.1 strain, which is adapted to MA-104 cells, and strain pABV437, which is the infectious cDNA clone of the field strain Ter Huurne is shown in (A). An overview of generated full length constructs based on pABV437 to observe the responsible mutations for the adaptation phenotype is shown in (B). The numbers in the bar correspond to the 9 open reading frames.

Materials and Methods.

Cells and Viruses.

Porcine alveolar lung macrophages (PAMs) were maintained in MCA-RPMI-1640 medium containing 5% FBS, 100 U/ml penicillin and 100 U/ml streptomycin. CL2621-cells were propagated in Eagle's minimal essential medium supplemented with Hanks salts (Gibco BRL), 10% FBS, 100 U/ml penicillin, 100 U/ml streptomycin, 1.5% sodium bicarbonate and 1% L-glutamine. Serial passage of the recombinant PRRSVs vABV688 and vABV437 was performed as described. (Meulenberg et al, 1998). Challenge virus LV-Ter Huurne, a virulent European wild type isolate of PRRSV, was isolated during the 1991 epizootic from a clinical case of PRRSV in the Netherlands and propagated on PAMs. (Wensvoort et al, 1991). SDSU# 73, a virulent American wild type isolate of PRRSV (passage 3 on CL2621-cells), was kindly provided by Dr. E. Vaughn (Boehringer Ingelheim, Animal Health, Ames, Iowa) and propagated on MA-104 cells. Virus titers (expressed as 50% tissue culture infective doses ($TCID_{50}$) per ml) were determined on PAMs by end point dilution (Wensvoort et al, 1986) and calculated according to Reed and Muench. (Reed et al, 1938).

Inoculation of pigs with PRRSV recombinants and test on their in vivo stability.

Three groups of three 8-week-old Dutch Landrace/Yorkshire (LY) SPF pigs, tested free of antibodies against PRRSV, were inoculated on the same day intranasally with 2 ml of a recombinant virus stock of passage 5 each containing a titer of $10^5$ $TCID_{50}$/ml. The three groups were housed in isolated pens. Experimental procedures and animal management procedures were undertaken according to the Dutch legislation animal experiments. Serum samples were collected at day 0, 2, 4, 7, 9, 11, 14, 16, 18 and 21. At day 21, the pigs were sacrificed.

Immunization of pigs with vABV688 and challenge with LV-Ter Huurne and SDSU#73.

For each recombinant virus, two groups of five 8-week-old Dutch LY SPF pigs, lacking antibodies against PRRSV, were immunized intramuscularly (half-way between the pinna of the right ear and the cranial ridge of the right shoulder blade) with 2 ml of a virus stock of $10^5$ TCID$_{50}$/ml. All groups were housed in isolated pens. Experimental procedures and animal management procedures were undertaken according to the Dutch legislation animal experiments. In order to determine the transmission of recombinant virus from the inoculated pigs, one naive sentinel pig was introduced into each group of inoculated pigs 24 hours post-vaccination and sacrificed 28 days thereafter. At day 28 post-vaccination, two animals were separated from one group of each mutant and challenged intranasally with 2 ml $10^5$ TCID$_{50}$/ml LV-Ter Huurne. Similarly, two animals were separated from the other group and challenged with 2 ml $10^5$ TCID$_{50}$/ml SDSU#73. The two challenged animals joined the other three vaccinates after 24 hours. At 28 days after challenge, all pigs were sacrificed.

Figure 1B:
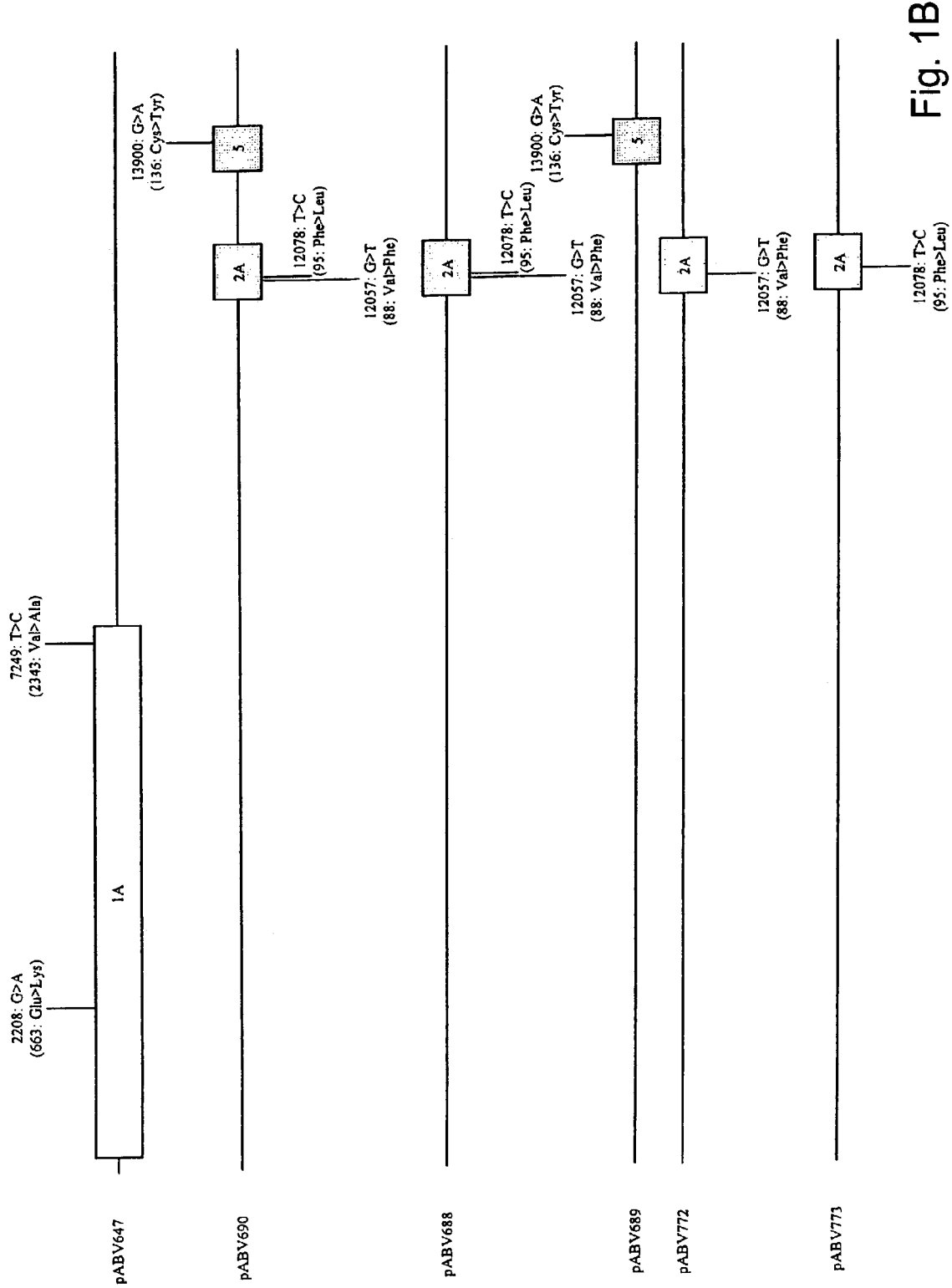

A schematic representation of the amino acid changes is depicted in FIGS. 1A and 1B. To confirm the efficacy of challenge, two non-inoculated animals were either inoculated intranasally with 2 ml $10^5$ TCID$_{50}$/ml LV-Ter Huurne or SDSU#73. These challenged animals joined three sentinel animals after 24 hours and were monitored for two weeks starting at the moment of challenge. Serum samples were collected for all animals three times a week starting on day 0. During the experiment, the animals were observed daily for signs of disease, i.e., fever (a rectal body temperature higher than 39.7° C.), diarrhea and respiratory distress.

Analysis of the genetic stability of the recombinant viruses.

The genetic stability of the recombinant viruses in pigs was tested by inoculation of PAMs with serum from these pigs taken at the last-virus-positive day, followed by sequence analysis of the viral RNA. In short, as soon as cytopathogenic effect (cpe) was detected, the culture supernatant was harvested and the viral RNA was isolated as described (16). The RNA was reverse transcribed with primer LV76 (5'-TCTAGGAATTCTAGACGATCG(T)$_{40}$-3' (SEQ ID NO: 1); antisense; nucleotide (nt) 15088). The region flanking the introduced mutations was amplified by PCR using primers LV9 (5'-CTGCCGCCCGGGCAAGT-GCC-3' (SEQ ID NO: 2); sense; nt 11746) and LV22 (5'-CATAATAACCCTCAAGTTG-3' (SEQ ID NO: 3); antisense; nt 12715) for vABV688. Nt numbers are based on the sequence of the LV isolate as deposited in GenBank, Accession number M96262 (SEQ ID NO: 4).

The amplified fragments were analyzed in 2% agarose gels and the PCR fragments were excised from the gel and purified with SpinX columns (Costar). Sequence analysis of the fragments was performed using the antisense primer of the PCR, except for vABV688, for which primer LV24 (5'-AATCGGATCCTCAGGAAGCGTGCACACT-GATGA-3' (SEQ ID NO: 5); antisense; nt 12419) was used. The PRISM Ready Dye Deoxy Terminator cycle sequencing kit and the ABI PRISM 310 Genetic Analyzer (Perkin Elmer) were used to determine the sequences.

Virus Isolation.

$10^5$ PAMs/96 mm$^2$ were seeded in 96-wells plates and after one day, 50 µl of a 10-fold and 100-fold serial dilution of each serum sample was used to infect PAMs. After 48 hours, 25 µl of the culture supernatant was transferred to new PAMs seeded 16-24 hours prior to incubation. After 24 hours, the medium was discarded, the cells were washed with 0.05 M NaCl, dried and frozen for IPMA. (Wensvoort, 1986).

Virus Titration.

Virus titers were determined by end-point dilution on PAMs. (Wensvoort et al., 1986). Samples containing virus titers below the detection level (1,8) were considered negative. From the area under the curve of titer against time, the integrated virus titers after vaccination were determined. Statistical analysis was performed by the one-sided paired student's t-test. Results were considered statistically significant when the P-value was ≦0.05.

Immunoperoxidase Monolayer Assay (IPMA).

Immunostaining of PAMs was performed according to the method described. (Wensvoort et al, 1986). The expression of the EU- and US-PRRSV N protein was detected with monoclonal antibody (MAb) 122.

Detection of Antibodies.

The presence of antibodies against PRRSV in pig sera was determined by ELISA (IDEXX, Westbrook, Minn., US).

EXAMPLE 1

Identification of Adaptation Sites.

To identify important genomic regions for adaptation, the field isolate Lelystad virus was passaged 6 times on CL2621 cells followed by plaque purification for 3 times on the CL2621 cells and the virus was designated LV4.2.1. The entire sequence of the genome of the cell line-adapted strain LV4.2.1 was determined. RNA isolation, RT-PCR and PCR was performed yielding overlapping cDNA fragments of about 1.5 kb in length. All fragments were cloned into pGEM-T vector of PROMEGA using the TA-cloning strategy. When sequencing the whole sequence, every nucleotide was determined at least twice. To exclude mutations introduced by PCR-mismatches, a third or even a fourth cDNA-construct was made. When compared to the field strain Lelystad virus, 27 nucleotide differences in the coding region were identified and no nucleotide differences were identified in the 5' and 3' non-translated region. After translation, 8 amino acid differences resulted (Table 1).

TABLE 1

Amino acid differences between LV4.2.1, the field virus Lelystad virus strain Ter Huurne, the infectious cDNA clone pABV437 and the US prototype field virus strain ATCC VR2332.

|  | ORFIA polyprotein | | | GP2A | | GP2B | GP5 |
|---|---|---|---|---|---|---|---|
|  | aa 663 | aa 1084 | aa 2343 | aa 29 | aa 88 | aa 95 | aa 27 | aa 136 |
| LV4.2.1 | Lys | Leu | Ala | Ser | Phe | Leu | Val | Tyr |
| Ter Huurne | Glu | Pro | Val | Pro | Val | Phe | Ala | Cys |

TABLE 1-continued

Amino acid differences between LV4.2.1, the field virus Lelystad virus strain Ter Huurne, the infectious cDNA clone pABV437 and the US prototype field virus strain ATCC VR2332.

| | ORFIA polyprotein | | | GP2A | | | GP2B | GP5 |
|---|---|---|---|---|---|---|---|---|
| | aa 663 | aa 1084 | aa 2343 | aa 29 | aa 88 | aa 95 | aa 27 | aa 136 |
| pABV437 | Glu | Pro | Val | Ser | Val | Phe | Val | Cys |
| ATCC-VR2332 | Gln | Thr | Val | Leu | Thr | Leu | Ile | Trp |

It was concluded that the observed difference in growth properties between LV4.2.1 and the field virus strain Lelystad virus was due to a different amino acid sequence in a non-structural protein, a structural protein or in a combination of two or more amino acid changes.

Construction of full length cDNA with non-structural or structural gene mutations.

A set of full length constructs (pABV647, 688, 689, and 690) was constructed based on pABV437 in which mutations were introduced. In vitro transcribed full length RNAs were transfected into the non-permissive BHK-21 cells using lipofectin as a cationic reagent. After 24 h, the supernatants (p0) were transferred to MARC-145 cells and after 24 h to 48 h, immunostaining was performed using MAb 122.17 directed against the N protein to detect the effect of the introduced mutations. Recombinant viruses containing substitutions responsible for adaptation showed cell line adapted phenotypes on MARC-145 cells similar to that of the positive control LV4.2.1. For the positive control, PAMs were infected with the same amount of p0 to show infection on the primary target cell of PRRSV. The supernatant p0 of pABV437 and LV4.2.1 virus served as positive controls in infection experiments.

Two full length cDNA clones were constructed in which either mutations in the non-structural or in the structural region were introduced and designated as pABV647 and pABV690, respectively (FIG. 1B). In vitro analysis of these two constructs revealed that the RNA-transcript of pABV690 resulted in a phenotype similar to LV4.2.1. It was concluded that the mutations responsible for adaptation are located in the structural part of the genome.

The next step was to determine whether the mutations in GP2a or in GP5 had any effect on the observed cell line-adaptation. pABV688 contains two amino acid differences in GP2a, while pABV689 contains only the amino acid change in GP5 (FIG. 1B). After performing the screening assay, pABV688 with the two mutations in GP2a resulted in a cell line-adapted phenotype similar to LV4.2.1 and the GP5 recombinant pABV689 did not. It was concluded that adaptation to the cell line is in majority caused by the two mutations in GP2a.

Full Length Genome Constructs with Mutations in GP2a.

Two amino acid differences in GP2a were studied. Two new constructs were generated. pABV772 contains a phenylalanine at amino acid 88 and pABV773 contains a leucine at position 95 in GP2a (FIG. 1B). In vitro, both substitutions were better adapted for growth in MARC-145 cells than the positive control pABV437, but the substitutions caused less cell pathologic effects (CPE) than vABV688.

A multi-step and a one-step growth curve were performed to investigate the effect of the introduced amino acid residues on the infectivity process. The p0-medium of the recombinant viruses derived from pABV437/688/772/773 were harvested, transferred to PAMs and passaged three times (p3) in parallel with LV4.2.1 to increase the amount of virus. For further growth characterization, the presence of the introduced mutations was confirmed by sequence analysis and the TCID50/ml was determined (data not shown). Multi-step growth curves on both PAMs and MARC-145 were performed using a multiplicity of infection (m.o.i) of 0.05 with vABV437/688/772/773 and LV4.2.1. $10^6$ cells were used in growth curves per 2 cm². At different time points, virus was harvested and stored until the virus titer in TCID50/ml was determined.

Figure 2C:
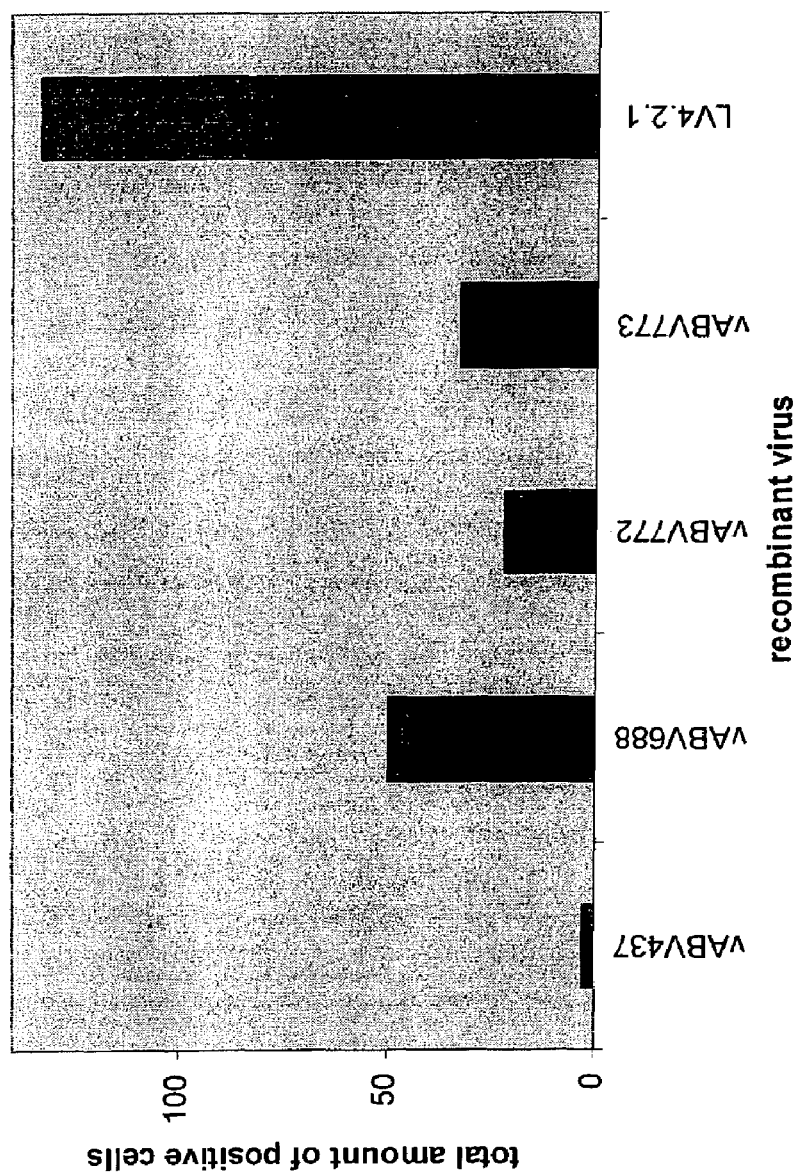
FIG. 2C: Immunostaining of infected cells using a PRRSV-specific Mab (122.17) against the nucleocapsid protein. The total amount of virus positive cells was counted per 2 $cm^2$.

Introduction of a phenylalanine and a leucine in GP2a at amino acid 88 and 95, respectively, had a positive effect on the growth characteristics of a European strain of PRRSV on MARC-145 cells (FIG. 2A). No differences were observed when performing multi-step growth curves on PAMs (FIG. 2B). To secure the observed results, a total amount of $10^6$ MARC-145 cells per 2 cm² were infected with a m.o.i. of 0.1 with supernatant p3 of vABV437/688/772/773 and LV4.2.1. After 12 h, an immunostaining was performed using a PRRSV-specific MAb (122.17) against the nucleocapsid protein and the total amount of positive cells were counted per 2 cm² (FIG. 2C). Based on the results, it was concluded that both amino acid residues at position 88 and 95 in the minor glycoprotein GP2a of PRRSV are important for adaptation to MARC-145 cells.

The arteriviral reproduction process in permissive cells can be defined in seven distinct steps. The first two processes are called the viral entry and include (A) attachment of the virus to the cell surface of PAMs or MA-104 (or derivatives thereof) and (B) penetration of the virus through the cell membrane. Next, (C) the arterivirus needs to be uncoated in the cytoplasm before (D) replication, transcription and translation can occur. The next step is (E) RNA encapsidation and assembly, followed by (F) release of mature virions into the extracellular space which occurs before (G) spread of the virus can take place. Using a 12 h-time point in the one-step growth curves and knowing that the viral reproduction cycle of PRRSV takes about 10 hours, the observed difference in the amount of positive stained cells is caused by an increased number of cells being successfully infected (A-D). The observed difference is not due to a difference in encapsidation of the RNA, release of the newly produced virions or spread of the virus through a monolayer of MARC-145 cells (E-G). Since a role of glycoprotein GP2a in release of viral RNA into the cytoplasm during uncoating (C) or in transcription and translation (D) is most unlikely, it was concluded that both residues, or a domain in which both residues are present, are important for the entry process, i.e., attachment and/or penetration of the virus (A and B).

EXAMPLE 2

Animal Experiments with Cell Line-Adapted Recombinant PRRSV vABV688.

In recombinant vABV688, amino acids 88 and 95 of the minor envelope glycoprotein GP2a were mutated and resulted in improved growth on MARC-145 cells. This characteristic facilitates the production of virus. In cell culture, these recombinant viruses were shown to be genetically stable and able to grow to virus titers sufficient to perform animal experiments. The properties of these PRRSV recombinants were studied with regard to safety and protective efficacy in animal experiments. The properties of the recombinant viruses were compared with those of virus derived from an infectious cDNA copy, vABV437. This virus is identical to wild type virus except for a PacI-restriction site and is, therefore, assumed to have similar properties as wild type virus. First, the in vivo genetic stability of vABV688 was determined in 8-week-old pigs. Subsequently, the immunogenicity, attenuation and efficacy of these viruses were tested in a homologous and heterologous immunization-challenge experiment in young pigs.

Genetic Stability of the PRRSV Recombinant vABV688 in 8-Week-Old Pigs.

In the first experiment, the genetic stability of the PRRSV recombinants was determined in vivo. Sequence analysis of viral RNA isolated from serum of all pigs inoculated from 14 days post inoculation (DPI) with the recombinant viruses at the last virus-positive day was performed. Sequence analysis of the fragments obtained by RT-PCR showed that the introduced mutations were present and that no additional changes were introduced in the domain of GP2a indicating that the recombinant viruses were genetically stable in vivo.

Seroconversion of Virus inoculated Pigs and Sentinel Pigs.

In the second experiment, it was determined whether pigs inoculated with the PRRSV recombinants and, subsequently, the sentinel pigs introduced into the inoculated groups had seroconverted. The presence of PRRSV antibodies was measured in IDEXX ELISA. Antibodies were detected in pigs inoculated with recombinant virus (i.e., ELISA sample-to-positive (S/P) ratio>0.4) which indicated proper exposure of the viruses to the animals. Virus transmission is one of the characteristics of virulence. The sentinels had seroconverted at day 14 (vABV688) indicating that transmission of virus from the inoculated animals to these sentinels and, thus, conservation of the virulence.

Duration and Height of Viremia after Inoculation.

Figure 3:
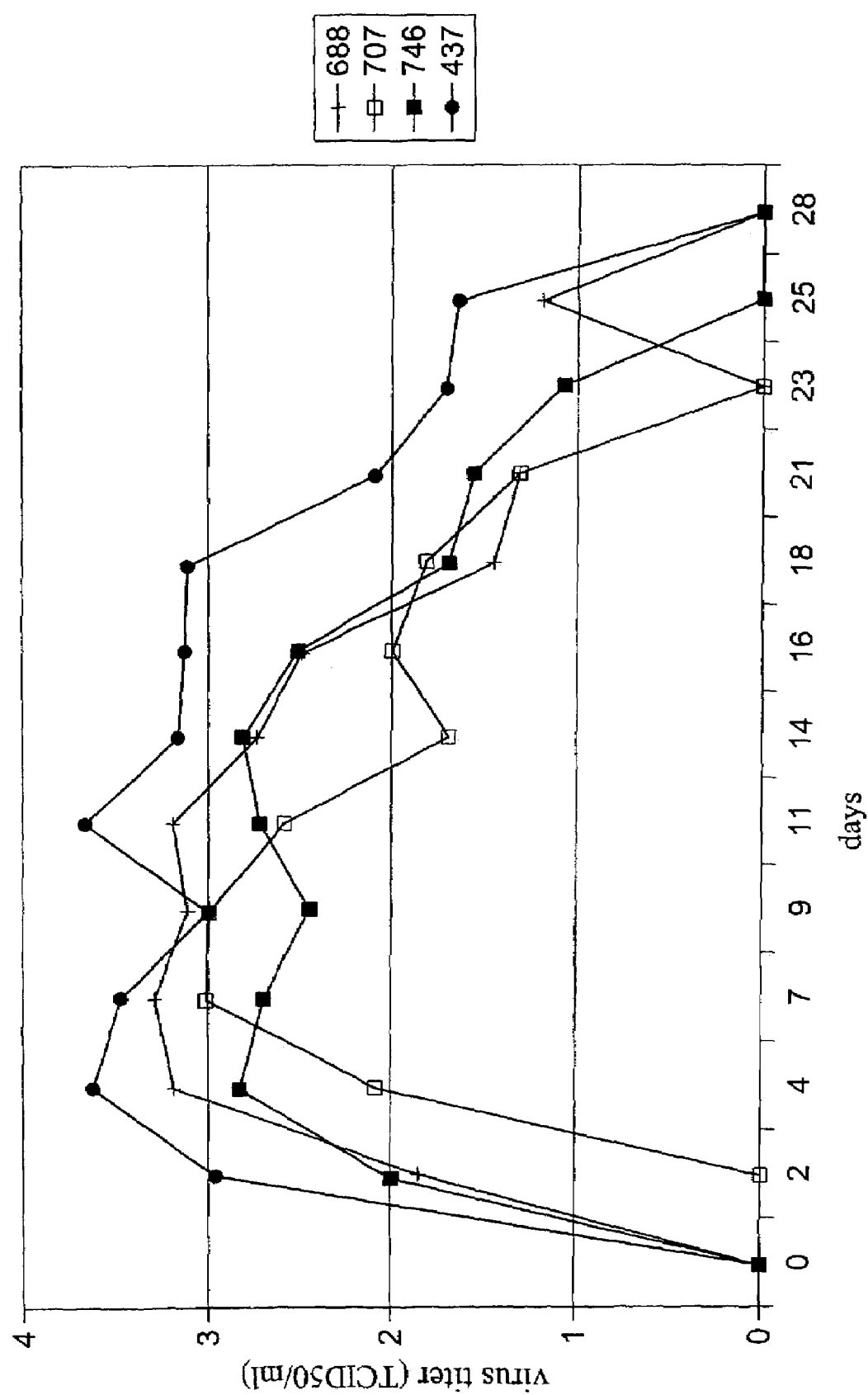
FIG. 3: Mean virus titer per group of pigs after inoculation with vABV688, vABV707, vABV746 and vABV437 as determined by end point dilution. Significance of the differences between the-virus groups ($p \leq 0.05$) was determined using the Chi test.

To determine the presence of virus in the serum of inoculated animals, virus isolation was performed for all sera collected. From the virus positive sera, virus titers were determined (FIG. 3). All viruses induced viremia in the pigs and ranged from 2 dpi to 25 dpi.

Viremia after Transmission of Virus to Sentinel Pigs.

To determine spread of the recombinant virus to non-inoculated pigs, one sentinel animal was introduced into each inoculated group at 24 hours after inoculation. The virus titration of all virus positive sera indicated that the maximum virus titers did not differ between inoculated pigs and sentinels (data not shown).

Challenge of virus-inoculated animals with homologous and heterologous PRRSV and transmission of challenge virus.

To test whether inoculation with the recombinant virus protects pigs against wild type PRRSV, the inoculated pigs were challenged with EU- and US-PRRSV. Pigs inoculated with vABV437 remained virus negative after challenge with LV-Ter Huurne. Only one animal of the vABV688-inoculated pigs became virus positive for one day. After challenge with SDSU#73, all inoculated animals became viremic. All inoculated, unchallenged animals remained virus negative after they were united with their group members that were challenged with LV-Ter Huurne. In pigs inoculated with vABV688, viremia was induced after the inoculated pigs were united with SDSU#73-challenged pigs. In pigs used as challenge control, viremia was induced in all LV-Ter Huurne and SDSU#78-challenged pigs as well as in all sentinel animals (data not shown).

Clinical Observations.

After inoculation with the virus, no severe clinical signs of the disease were monitored. Only moderate rectal temperature increases were noted in all inoculated groups (data not shown). After challenge with LV-Ter Huurne in vABV688-inoculated animals and all SDSU#73-challenged animals, no temperature increases were measured.

EXAMPLE 3

Attenuation of PRRS mutant virus strains with mutations in GP5 and/or ORF1ab in addition to the mutations in GP2a (LV4.2.1). Comparison of virulence of 3 PRRS virus strains in an animal model.

The clinical signs of PRRSV may differ among strains after exposure of pigs to PRRSV. The US PRRSV strains often cause respiratory and reproductive problems, whereas EU PRRSV strains predominantly cause reproductive problems. (Steverink et.al. 1999). Respiratory signs and the extent of lung involvement may vary per strain and are not consistently reproduced under experimental conditions. An infection model should include parameters to study and quantify the virulence of the virus based on frequency and severity of clinical signs, viral parameters (viremia, virus excretion and virus transmission) and seroconversion. Furthermore, duration, height and frequency of viremia and viral excretion after vaccination could also be important parameters to study vaccine safety. The same parameters after PRRSV challenge of vaccinated animals are important for vaccination efficacy since reducing virus shedding and virus transmission among pigs is an important target aiming at the control of PRRSV. Therefore pigs of 6 to 8 weeks old and 6 months old were infected with 3 different PRRSV strains, i.e., LV-Ter Huurne, SDSU#73 and LV4.2.1.

The animals were conventional Landrace pigs obtained from a PRRSV-free farm in Denmark and born from PRRSV-unvaccinated sows. The pigs were free from antibodies against PRRSV as measured by an ELISA (IDEXX). Viremia was first detected in all pigs at 3 dpi except for the 6 month-old group infected with LV4.2.1 where viremia was first detected at 7 dpi and in one animal of this group, no viremia was detected. In 6-8 week-old pigs, viremia was detected until 42 dpi with a maximum frequency of positive animals of 88% and a virus titer ranging from 3, 4, 7, 10, 11 or 14 dpi and from 2.1-2.6.

In 6 month-old pigs, viremia was detected until 28 dpi with a maximum frequency of 65% positive animals per time-point and virus titer ranging from 0.7-1. After 24 dpi, both LV-Ter Huurne and SDSU#73 were intermittently detected in the serum of pigs. LV4.2.1-infected pigs showed a shorter duration of viremia which was last detected at 21 dpi. The frequency of positive pigs at 7 and 10 dpi was significantly lower, had a maximum of 41% (p>0.05) and a lower $^{10}$log virus titer as compared to LV-Ter Huurne and SDSU#73. Kinetics of viremia was significantly different at 14 dpi for LV-Ter Huurne-infected pigs and SDSU#73-infected pigs.

More pigs of 6-8 weeks excrete virus (maximum of positive animals per time-point was 50%) than pigs of 6 months (maximum of 37%). Furthermore, 6-8 week-old pigs showed a higher virus $^{10}$log titer (between 0.2 and 1.9) in tonsillar swabs than 6 month-old pigs (ranging from 0.0 to 0.3) at day 3, 4, 7, 10 or 11 and 14. Per time-point, more pigs infected with LV-Ter Huurne excrete virus (maximum 100%) as compared to LV4.2.1 (maximum 17%) and SDSU#73 (maximum 50%). In addition, all pigs infected with LV-Ter Huurne excreted virus, but not all pigs infected with LV4.2.1 or SDSU#73 excreted virus. The $^{10}$log virus titer in tonsillar swabs was higher for LV-Ter Huurne-infected pigs ranging from 0.0 to 3.0, while the $^{10}$log titer of the LV4.2.1 infected group was 0.0 and the $^{10}$log titer of the SDSU#73 infected pigs ranged from 0.0 to 0.5. At 14 dpi, pigs were still excreting virus.

LV-Ter Huurne and SDSU#73 appear to be the most virulent due to the occurrence of a high level of virus-positive pigs, a long duration of viremia of both virus strains, the instigation of most severe clinical signs of SDSU#73 and a high level of virus excretion for LV-Ter Huurne. LV4.2.1 was less virulent since it showed less clinical signs and a low viremia and virus excretion. The reduced virulence of LV 4.2.1 was confirmed by impairment in its ability to cause reproductive problems for gestation sows as compared to LV-Ter Huurne. (Steverink et al. 1999). Sows infected with LV-Ter Huurne and LV4.2.1 resulted in the same number of piglets, but the piglets of the sows infected with the higher virulent strain were weaker. In addition, the group infected with the higher virulent virus LV-Ter Huurne showed a higher frequency of virus positive piglets until 28 days post farrowing. (Steverink et al 1999). Apparently, the lower virulence of LV4.2.1 is not related to macrophage infection since the growth curve of LV4.2.1 in vitro on macrophages is comparable to the growth curve of LV-Ter Huurne.

REFERENCES

Bautista, E. M., Goyal, S. M., Yoon, I. J., Joo, H. S. & Collins, J. E. (1993). Comparison of porcine alveolar macrophages and CL 2621 for the detection of porcine reproductive and respiratory syndrome (PRRS) virus and anti-PRRS antibody. J Vet Diagn Invest 5, 163-5.

Collins, J. E., Benfield, D. A., Christianson, W. T., Harris, L., Hennings, J. C., Shaw, D. P., Goyal, S. M., McCullough, S., Morrison, R. B., Joo, H. S. & et al. (1992). Isolation of swine infertility and respiratory syndrome virus (isolate ATCC VR-2332) in North America and experimental reproduction of the disease in gnotobiotic pigs. J Vet Diagn Invest 4, 117-26.

Duan, X., Nauwynck, H. J., Favoreel, H. W. & Pensaert, M. B. (1998). Identification of a putative receptor for porcine reproductive and respiratory syndrome virus on porcine alveolar macrophages. J Virol 72, 4520-3.

Jusa, E. R., Inaba, Y., Kouno, M. & Hirose, O. (1997). Effect of heparin on infection of cells by porcine reproductive and respiratory syndrome virus. Am J Vet Res 58, 488-91.

Kreutz, L. C. (1998). Cellular membrane factors are the major determinants of porcine reproductive and respiratory syndrome virus tropism. Virus Res 53, 121-8.

Meulenberg, J. J., Bos de Ruijter, J. N., van de Graaf, R., Wensvoort, G. & Moormann, R. J. (1998). Infectious transcripts from cloned genome-length cDNA of porcine reproductive and respiratory syndrome virus. J Virol 72, 380-7.

Reed L J, Muench H. A simple method of estimating fifty percent end points. Am J Hyg 1938;27: 709-16.

Snijder, E. J. & Meulenberg, J. J. (1998). The molecular biology of arteriviruses. J Gen Virol 79, 961-79.

Wensvoort G, Terpstra C, Boonstra J, Bloemraad M, Van Zaane D. Production of monoclonal antibodies against swine fever virus and their use in laboratory diagnosis. Vet Microbiol 1986;12: 101-8.

Wensvoort, G., de Kluyver, E. P., Luijtze, E. A., den Besten, A., Harris, L., Collins, J. E., Christianson, W. T. & Chladek, D. (1992). Antigenic comparison of Lelystad virus and swine infertility and respiratory syndrome (SIRS) virus. J Vet Diagn Invest 4, 134-8.

Wensvoort, G., Terpstra, C., Pol, J. M., ter Laak, E. A., Bloemraad, M., de Kluyver, E. P., Kragten, C., van Buiten, L., den Besten, A., Wagenaar, F. & et al. (1991). Mystery swine disease in The Netherlands:the isolation of Lelystad virus. Vet Q 13, 121-30.

Steverink, P. J. G. M., Pol, J. M. A., Bos-De Ruijter, J. N. A. & Meulenberg, J. J. M. Virulence of vABV414, the virus derived from the infectious cDNA clone of Lelystad virus, for third trimester pregnant gilts. Proc. PRRS & Aujeszky's disease 1999, 119.

What is claimed is:

1. A method for increasing the capability of an Arterivirus to replicate in a permissive cell, said method comprising:
    determining amino acids of the Arterivirus at positions that correspond to amino acid positions 75-107 of GP2a (SEQ. ID. NO. 6) of PRRSV isolate I-1102; and
    changing at least one of the determined amino acids of the Arterivirus to a different amino acid, wherein at least one of the determined amino acids of the Arterivirus corresponds to position 88 of GP2a of PRRSV isolate I-1102, and wherein the determined amino acid of the Arterivirus that corresponds to position 88 of GP2a of PRRV isolate I-1102 is changed from a valine to another amino acid.

2. The method according to claim 1, wherein the determined amino acid of the Arterivirus that corresponds to position 88 of GP2a of PRRV isolate I-1102 is changed from valine to phenylalanine.

3. The method according to claim 1, wherein the permissive cell is a green monkey cell.

* * * * *